United States Patent [19]
Gilbert et al.

[11] Patent Number: 5,674,876
[45] Date of Patent: Oct. 7, 1997

[54] p-HETEROATOM-SUBSTITUTED PHENOLS AND USES THEREOF

[75] Inventors: John C. Gilbert; Kimberly Kline; Kathiresan Krishnan; Maria Simmons Menchaca; Marian Pinto; Robert G. Sanders, all of Austin, Tex.

[73] Assignee: Research Development Foundation, Carson City, Nev.

[21] Appl. No.: 375,633

[22] Filed: Jan. 20, 1995

[51] Int. Cl.$^6$ .............. A61K 31/47; A61K 31/34; A61K 31/40; C07D 209/26; C07D 455/04
[52] U.S. Cl. .............. 514/294; 514/212; 514/214; 514/415; 514/469; 514/470; 540/461; 540/479; 540/523; 546/94; 548/491; 548/510; 549/466; 549/471
[58] Field of Search .............. 546/94, 157; 514/294, 514/415, 469, 470, 212, 214; 548/510, 491; 540/461, 479, 523; 549/466, 471

[56] References Cited

FOREIGN PATENT DOCUMENTS

| | | |
|---|---|---|
| 50-157369 | 12/1975 | Japan. |
| 55-006321 | 1/1980 | Japan. |
| 61-134387 | 6/1986 | Japan. |
| 2-194062 | 7/1990 | Japan. |
| 3-293673 | 12/1991 | Japan. |
| 94/08930 | 4/1994 | WIPO. |

OTHER PUBLICATIONS

Barclay et al., "Chain–Breaking Phenolic Antioxidants: Steric and Electronic Effects in Polyalkylchromanols, Tocopherol Analogs, Hydroquinones, and Superior Antioxidants of the Polyalkylbenzochromanol and Naphthofuran Class", *J. Org. Chem.*, 1993, 58, 7416–7420.

DeVita VT, Hellman S, Rosenberg SA. Cancer. Principles and Practice of Oncology. Lippencott. Philadelphia. pp. 144–145. 1985.

Sof'ina, Goldin, Belousova. Experimental Evaluation of Antitumor Drugs in USA and USSR and Clinical Correlations. NIH Publication No. 80-1993. pp. 76–78. 1980.

Svensson KG, Nilsson JLG. Acta. Pharm. Suec. 10 (4), 277–84. 1973.

Kucklaender, U and Henze U. Arch. Pharm. 317(5) 394–403 (1984).

Katayama H. Abe E. and Kaneko K. J. Heterocycl. Chem. 19(4) 925–6 (1982).

Burton G.W., Doba T, Gabe EJ, Hughes L, Lee FL, Prasad L, Ingold KU. (1985) J. Am. Chem. Soc. 107 (24) 7053–7065.

*Primary Examiner*—C. Warren Ivy
*Assistant Examiner*—Evelyn Huang
*Attorney, Agent, or Firm*—Benjamin Aaron Adler

[57] ABSTRACT

The present invention provides an antiproliferative p-heteroatom-substituted phenol compound having the structure formula

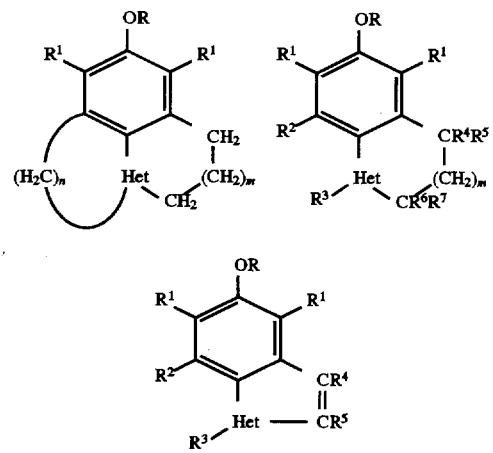

wherein m is 0 to 3, n is 0 to 4 when Het is nitrogen, wherein R is selected from the group consisting of hydrogen, alkyl, arylmethyl and acyl; $R^1$ is alkyl; $R^2$ is selected from the group consisting of hydrogen and alkyl; $R^3$ is selected from the group consisting of alkyl and acyl when Het is nitrogen, $R^4$ is selected from the group consisting of hydrogen and alkyl; $R^5$ is selected from the group consisting of hydrogen and alkyl; and $R^6$ and $R^7$ are selected from the group consisting of hydrogen, alkyl and $R^6$ and $R^7$ together may represent oxygen. Also provided are various methods for the treatment of a pathological cell proliferative disease comprising administering to an animal) a pharmacologically and therapeutically effective dose of a pharmaceutical composition comprising a p-heteroatom-substituted phenols or an analog thereof.

17 Claims, 10 Drawing Sheets m = 0–3
n = 0 when Het = O or S, 0–4 when Het = N
Het = N, O, or S,
R = H, alkyl, arylmethyl, or acyl
$R^1$ = alkyl
$R^2$ = H or alkyl
$R^3$ = alkyl or acyl when Het = N;
  = : when Het = O or S
$R^4$ = H or alkyl
$R^5$ = H or alkyl
$R^6$ = $R^7$ = H, alkyl, or =O Reagents: a. $(CH_3)_2SO_4$, NaOH; b. conc. $HNO_3$; c. 10% Pd/C, $H_2$, EtOH; d. $Cl(CH_2)_3Br$, $Na_2CO_3$, molecular sieves; e. conc. HBr; f. $Ac_2O$, $Et_3N$ Reagents. a. Ac₂O, AcOH; b. Br₂/AcOH; c. NaH/THF; d. Allyl bromide; e. (nBu)₃SnH, AIBN/Toluene; f. LiEt₃BH/THF; g. conc. HBr; h. pH > 7; i. BBr₃; j. RC(=O)Cl, Pyr./CH₂Cl₂; k. Ac₂O, Pyr.; l. NaH, MeI/THF Reagents. a. BrCH$_2$C(CH$_3$)=CH$_2$, NaH/THF; b. Pd(OAc)$_2$, Ph$_3$P, Et$_4$NCl, NaOCHO/DMF; c. BBr$_3$/CH$_2$Cl$_2$ Reagents. a. (CH₃)₃CC(=O)Cl, Pyr./CH₂Cl₂; b. Br₂/AcOH; c. BrCH₂C(CH₃)=CH₂, NaH/THF; d. Pd(OAc)₂, Ph₃P, Et₄NCl, NaOCHO/DMF; e. conc. HBr Reagents. a. $Na_2S_2O_4$; b. NaH, $BrCH_2CH=CH_2$/THF; c. $CH_3C(=O)N(Si(CH_3)_3)_2$; d. $BCl_3$; e. $Ac_2O$, Pyr.; f. (i) $O_3$, -78 °C/$CH_3OH$, $CH_2Cl_2$ (ii) $(CH_3)_2S$; g. Jones' reagent/acetone; h. (i) $K_2CO_3$/MeOH (ii) pH<7

Reagents. a. $H_2NOH \cdot HCl/EtOH$; b. $Na_2S_2O_4$, NaOH; c. $(CH_3)_3CC(=O)Cl$, Pyr.; d. $Ac_2O$, $Et_3N/CH_2Cl_2$; e. $Br_2$, $I_2/HOAc$; f. $K_2CO_3/CH_3OH$; g. $(CH_3)_3CSi(CH_3)_2Cl$; imidazole/DMF; h. NaH, $BrCH_2CH=CH_2/THF$; i. $Pd(OAc)_2$, $Ph_3P$, $Et_4NCl$, NaOCHO/DMF Reagents. a. Ac$_2$O, Pyr.; b. Br$_2$, Fe/HOAc; c. NaH, BrCH$_2$CH=CH$_2$/DMF; d. (n-Bu)$_3$SnH AIBN/Toluene; e. K$_2$CO$_3$/CH$_3$OH Reagents. a. NaH, BrCH$_2$C(CH$_3$)=CH$_2$/DMF; b. Pd(OAc)$_2$, Ph$_3$P, Et$_4$NCl, NaOCHO/DMF; c. K$_2$CO$_3$/CH$_3$OH

ρ-HETEROATOM-SUBSTITUTED PHENOLS AND USES THEREOF

BACKGROUND OF THE INVENTION

1. Field of the Invention

The present invention relates generally to the fields of organic chemistry and novel inhibitors of cell proliferation. More specifically, the present invention relates to novel p-heteroatom-substituted phenols and analogs thereof, and their use as antiproliferative agents.

2. Description of the Related Art

The control of cell proliferation is a complex process that involves multiple interacting components. Whether a cell grows or not depends on the balance of the expression of negatively-acting and positively-acting growth regulatory genes. Negatively-acting growth regulatory genes are those that, when expressed in or provided to a cell, lead to suppression of cell growth. Positively-acting growth regulatory genes are those which, when expressed in or provided to a cell, stimulate its proliferation. Recently, several negatively-acting growth regulatory genes, called tumor suppressor genes, which have a negative effect on cell proliferation have been identified. These genes include, but are not limited to, the human retinoblastoma gene, RB-1, and the p53 gene. The absence or inactivation of some of these negative growth regulatory genes has been correlated with certain types of cancer.

There is a wide variety of pathological cell proliferative conditions for which novel methods are needed to provide therapeutic benefits. These pathological conditions may occur in almost all cell types capable of abnormal cell proliferation. Among the cell types that exhibit pathological or abnormal growth are (1) fibroblasts, (2) vascular endothelial cells, and (3) epithelial cells. It can be seen from the above that methods are needed to treat local or disseminated pathological conditions in all or almost all organ and tissue systems of the individual.

Melanoma, the most virulent of skin cancers, is a highly metastatic disease affecting both sexes and is almost uniformly fatal within five years of diagnosis. Surgical removal of localized malignancies has proven effective only when the disease has not spread beyond the primary lesion. Once the disease has spread, the surgical procedures must be supplemented with other more general procedures to eradicate the diseased or malignant cells. Most of the commonly utilized supplementary procedures such as irradiation or chemotherapy are not localized to the tumor cells and, although they have a proportionally greater destructive effect on malignant cells, often affect normal cells to some extent.

Sterically hindered phenols are an important class of peroxyl trapping antioxidants in both biological and non-biological environments. For example, α-tocopherol, a component of vitamin E, is the major lipid soluble antioxidant in human blood, and its biological function, as well as that of its analogs, continues to be of considerable interest. The structural features responsible for the high antioxidant activity of α-tocopherol and its analogs are known, at least as measured in homogeneous solution, and numerous papers discuss determination of rate constants, $k_1$, for the chain-terminating reaction of phenols with peroxyl radicals (eq. 1). Complementary studies have been reported in micellar systems and more recently in environments designed to model biological membranes.

$$ROO\cdot + ArOH \xrightarrow{k_1} ROOH + ArO\cdot \quad (1)$$

The relative efficacies of the phenolic antioxidants, as reflected in $k_1$, as well as the absolute values of these rate constants, are media dependent. The major factor defining the free radical chain-terminating activity of the phenols is the nature of the substitution on the aromatic ring. Ortho-, meta-, and para-alkyl, para-alkoxy, and para-alkylthio groups are seen to augment the reactivity of the phenols toward radicals, owing to stabilization of the incipient phenoxyl radical character of the transition state for hydrogen atom transfer. Epr studies have confirmed that the heteroatom-containing substituents interact with the unpaired spin in the phenoxyls. Moreover, stereo-electronic effects appear to be important in the case of alkoxy and alkylthio groups.

The prior art is deficient in the lack of effective means of inhibiting the undesirable or uncontrollable cell proliferation in a wide variety of pathophysiological conditions. The present invention fulfills this long-standing need and desire in the art.

SUMMARY OF THE INVENTION

In one embodiment of the present invention, there are provided antiproliferative p-heteroatom-substituted phenolic compounds, or derivatives thereof, having a structural formula selected from the group consisting of

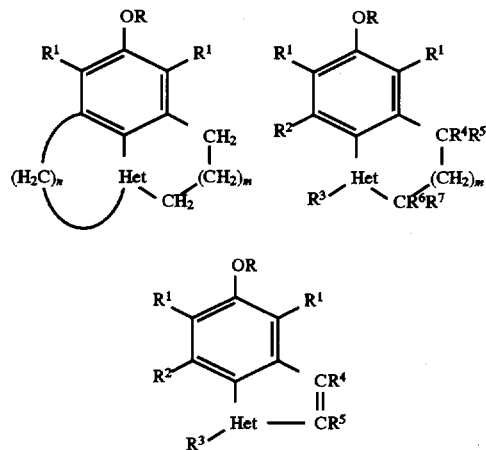

wherein m is 1 to 3, n is 0 when Het is oxygen or sulfur, 0 to 4 when Het is nitrogen, Het is nitrogen, oxygen or sulfur; wherein R is selected from the group consisting of hydrogen, alkyl, arymethyl and acyl; $R^1$ is alkyl; $R^2$ is selected from the group consisting of hydrogen and alkyl; $R^3$ is selected from the group consisting of alkyl and acyl when Het is nitrogen, :(electron pair) when Het is oxygen or sulfur; $R^4$ is selected from the group consisting of hydrogen and alkyl; $R^5$ is selected from the group consisting of hydrogen and alkyl; and $R^6$ and $R^7$ are selected from the group consisting of hydrogen, alkyl and oxygen.

In another embodiment of the present invention, there is provided a pharmaceutical composition comprising the compound of claim 1 and a pharmaceutically acceptable carrier.

In yet another embodiment of the present invention, there is provided a method for the treatment of a pathological cell proliferative disease comprising administering to an animal a pharmacologically and therapeutically effective dose of a pharmaceutical composition comprising a p-heteroatom-substituted phenol or an analog thereof.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

Figure 1:
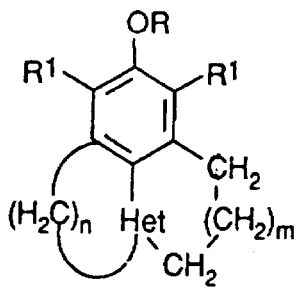
FIG. 1 shows the structures of the antiproliferative p-heteroatom-substituted phenolic compounds, or derivatives thereof, of the present invention.
Figure 1:
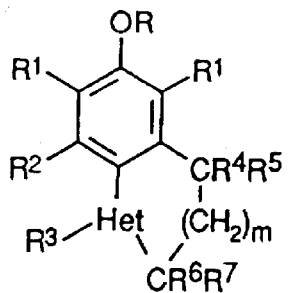
Figure 1:
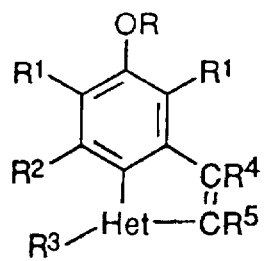
Figure 2:
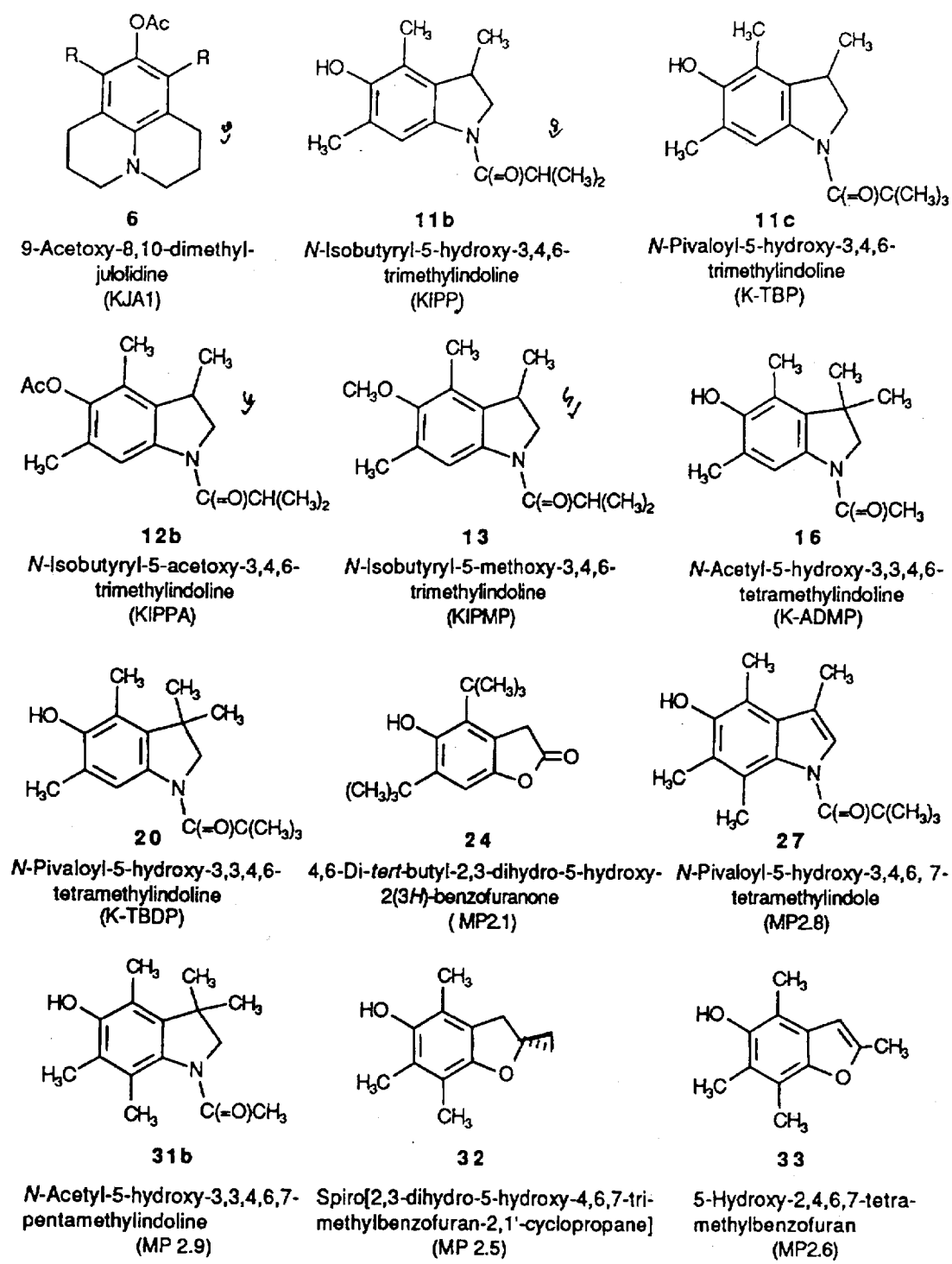
FIG. 2 shows individual structures and compound names for selected antiproliferative p-heteroatom-substituted phenol, or derivative sthereof, compounds of the present invention.
Figure 3:
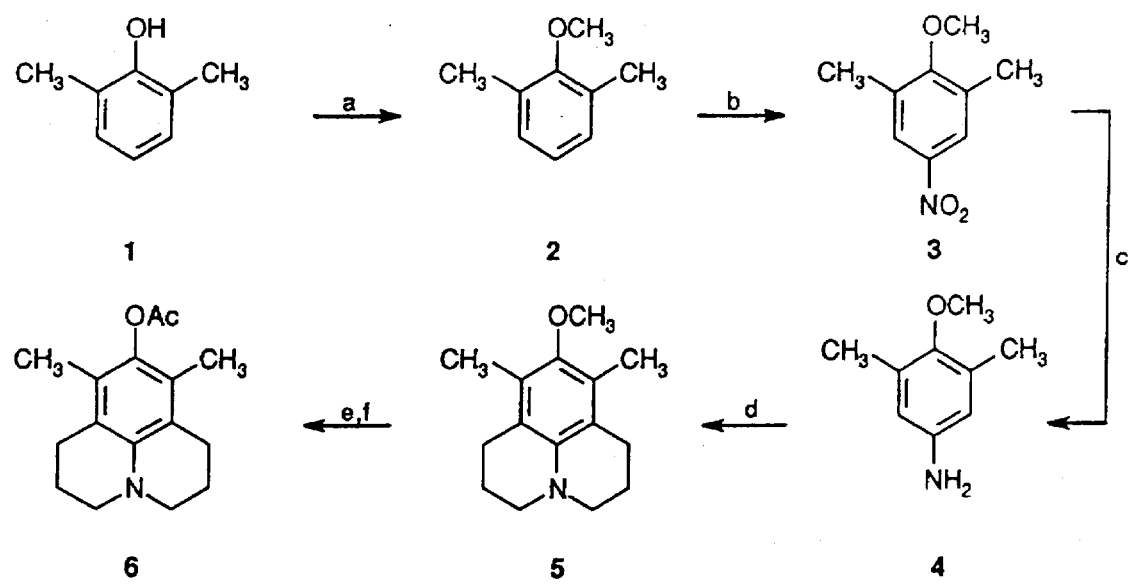
FIG. 3 shows the synthetic scheme for the synthesis of 9-acetoxy-8,10-dimethyljulolidine (6).
Figure 4:
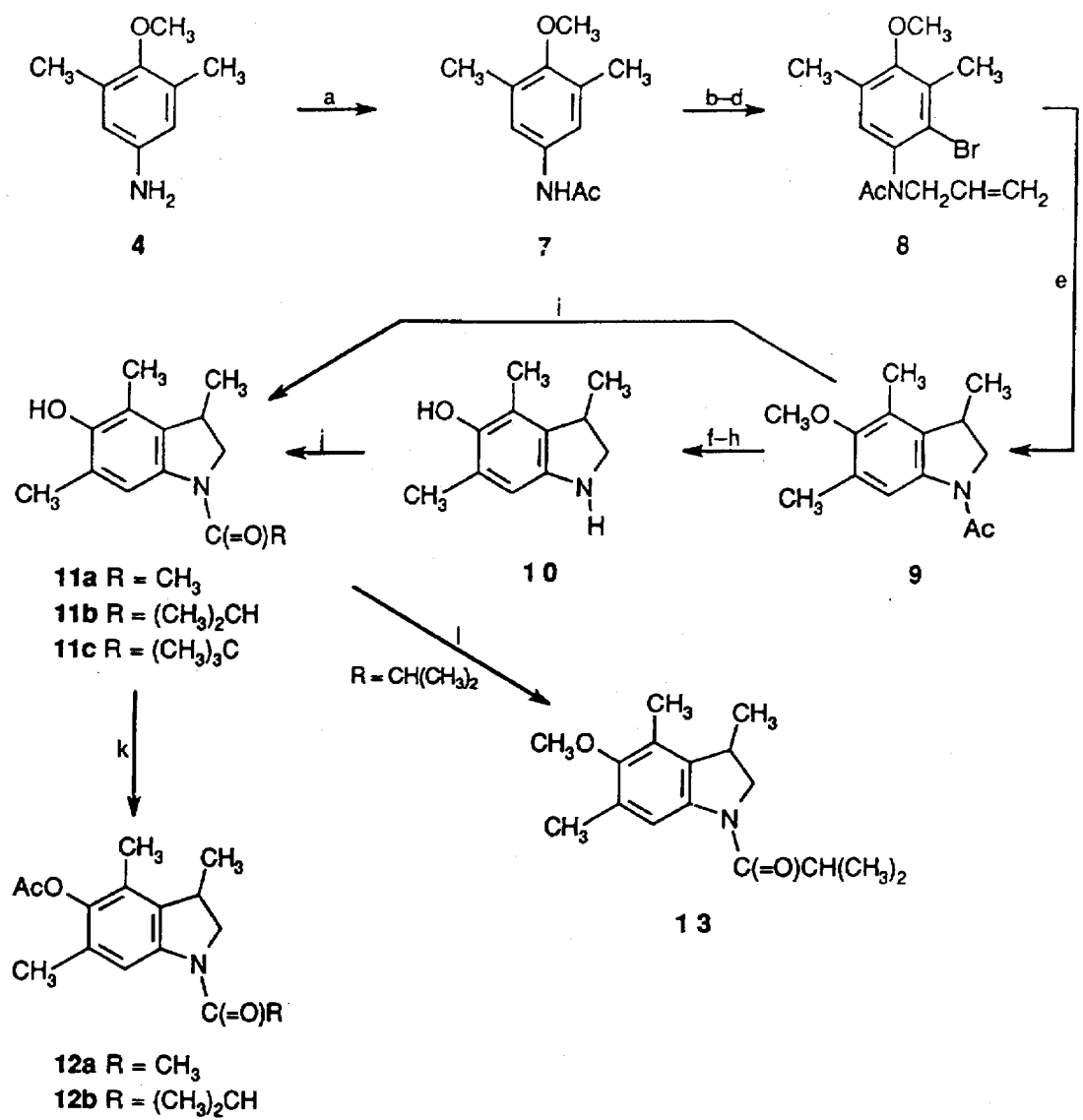
FIG. 4 shows the synthetic scheme for the synthesis, among others, of N-isobutyryl-5-hydroxy-3,4,6-trimethylindoline (lib), N-pivaloyl-5-hydroxy-3,4,6-trimethylindoline (11c), N-isobutyryl-5-acetoxy-3,4,6-trimethylindoline (12b), and N-isobutyryl-5-methoxy-3,4,6-trimethylindoline (13).
Figure 5:
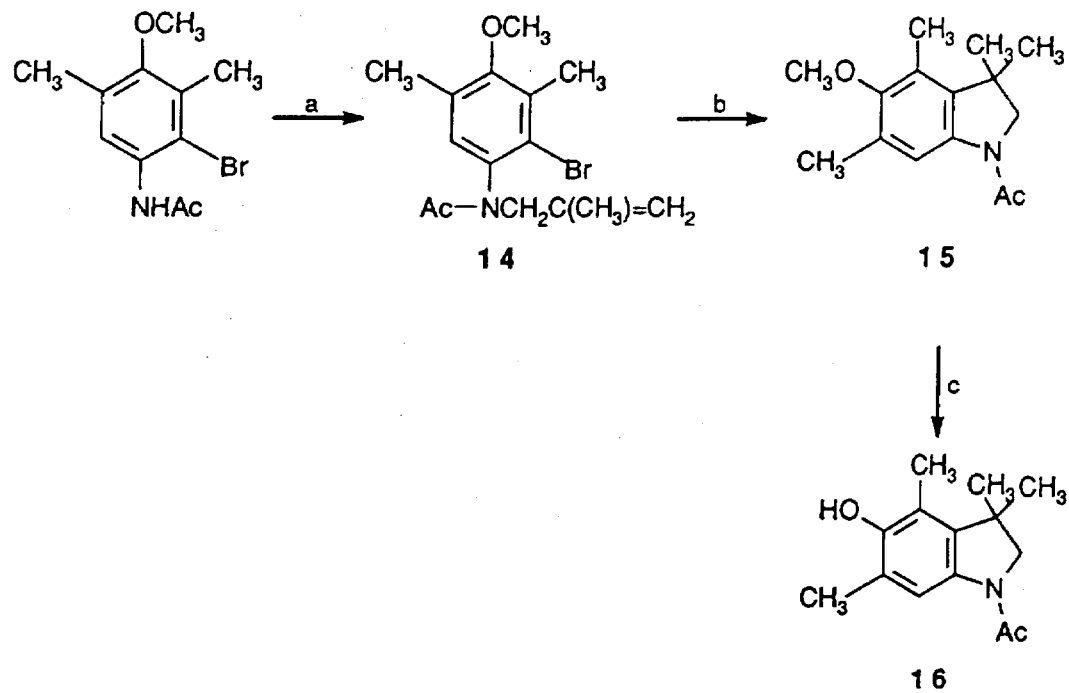
FIG. 5 shows the synthetic scheme for the synthesis of N-acetyl-5-hydroxy-3,3,4,6-tetramethylindoline (16).
Figure 6:
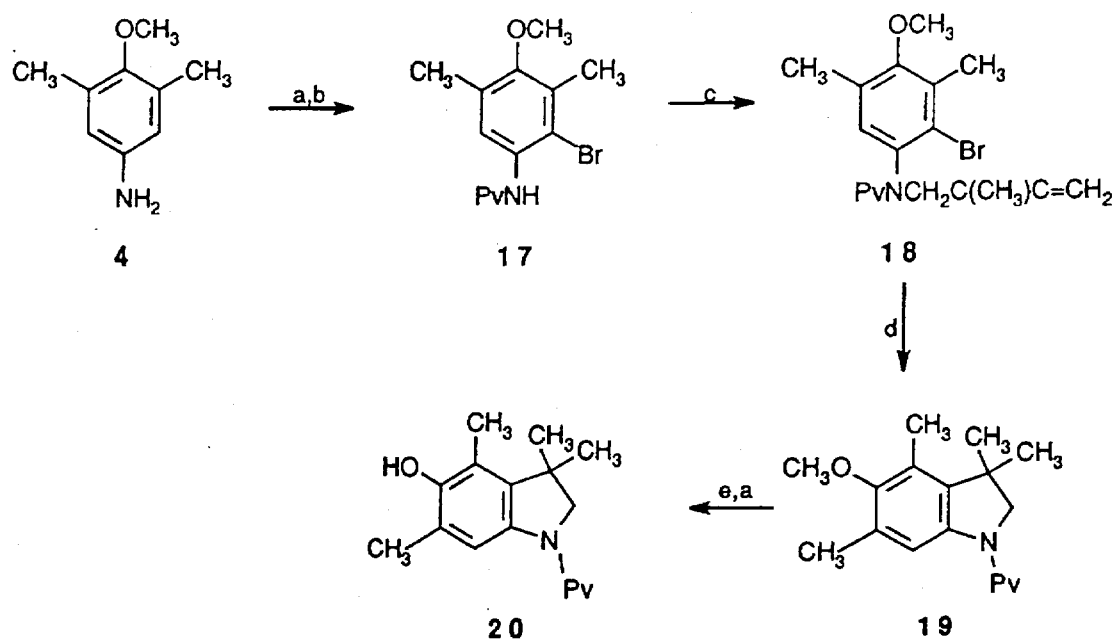
FIG. 6 shows the synthetic scheme for the synthesis of N-pivaloyl-5-hydroxy-3,3,4,6-tetramethylindoline (20).
Figure 7:
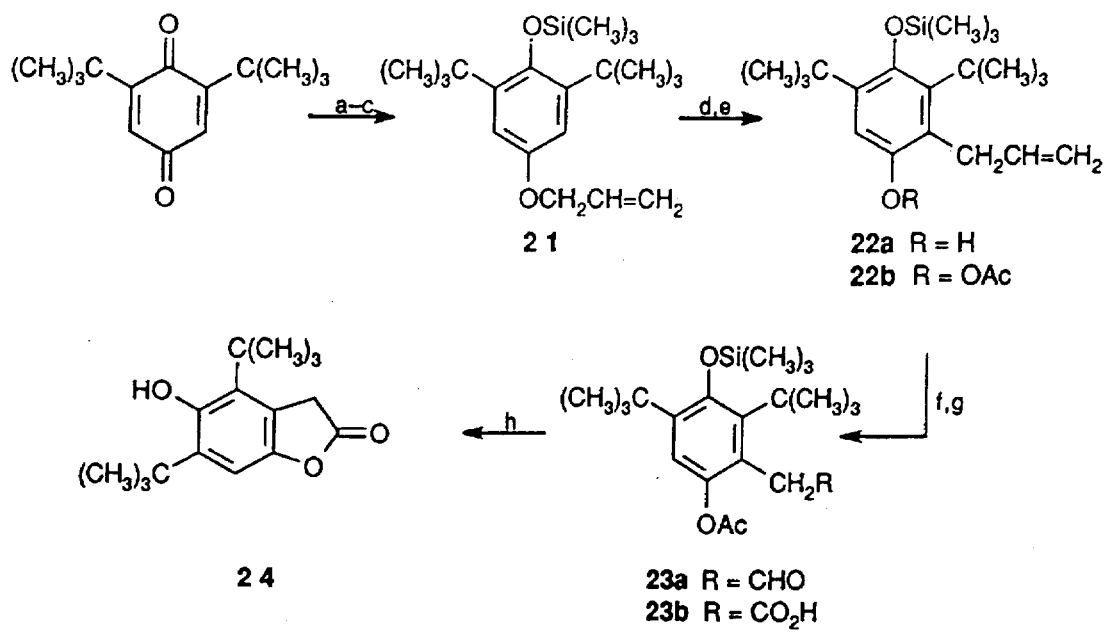
FIG. 7 shows the synthetic scheme for the synthesis of 4,6-di-tert-butyl-2,3-dihydro-5-hydroxy-2(3H)-benzofuranone (24).
Figure 8:
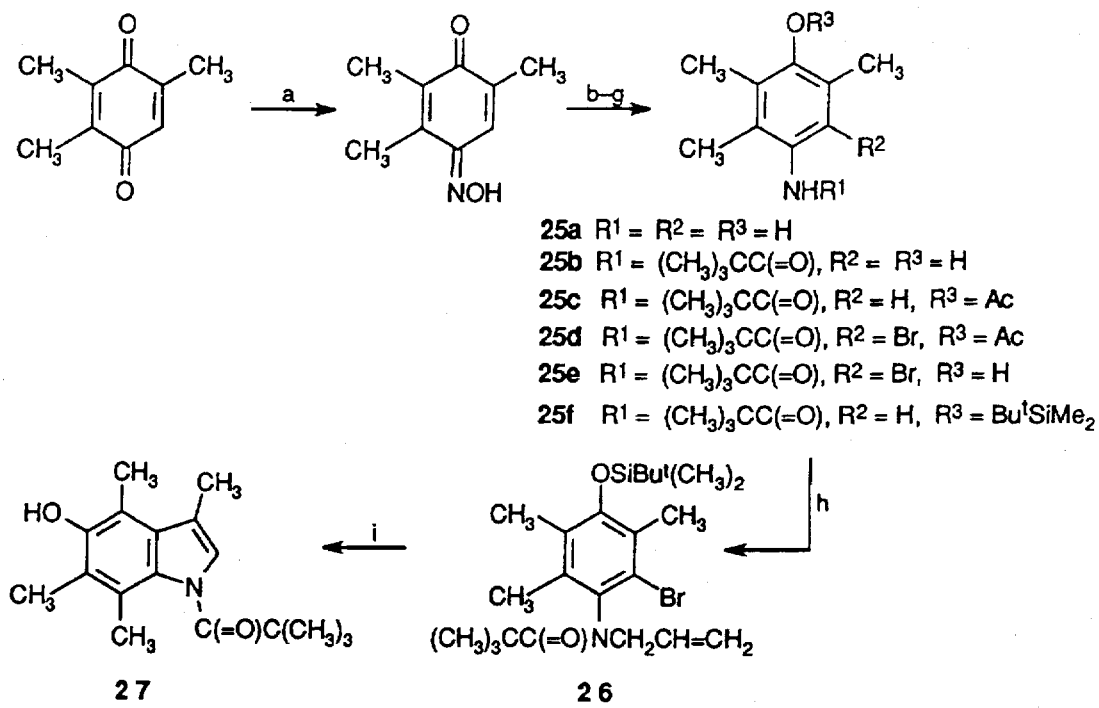
FIG. 8 shows the synthetic scheme for the synthesis of N-pivaloyl-5-hydroxy-3,4,6,7-tetramethylindole (27).
Figure 9:
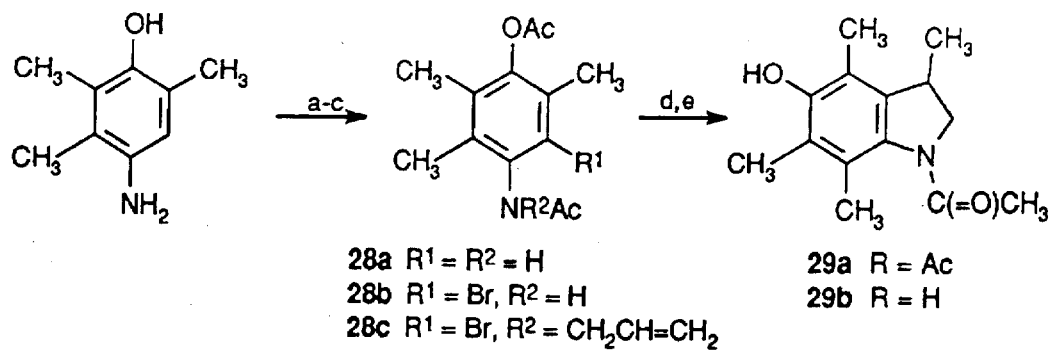
FIG. 9 shows the synthetic scheme for the synthesis of N-acetyl-5-hydroxy-3,4,6,7-tetramethylindoline (29b)
Figure 10:
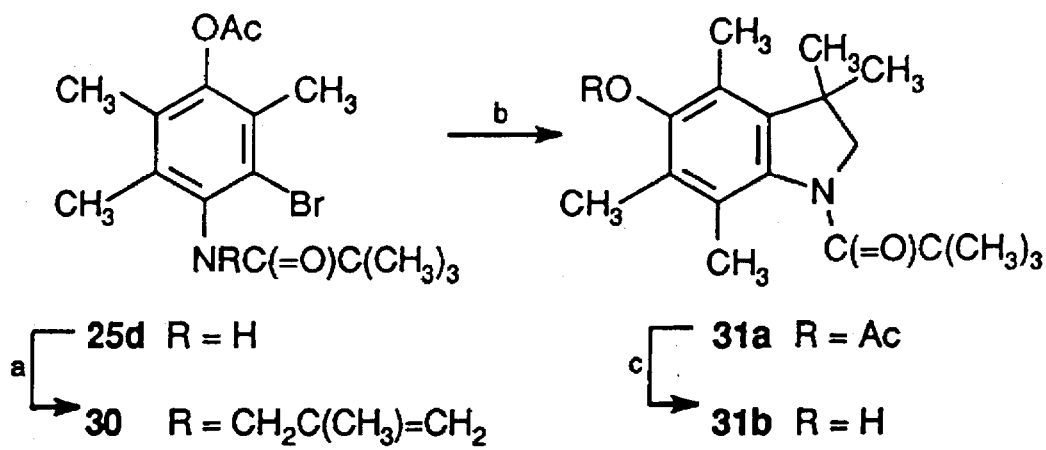
FIG. 10 shows the synthetic scheme for the synthesis of N-acetyl-5-hydroxy-3,3,4,6,7-pentamethylindoline (31b)

The present invention provides p-heteroatom-substituted phenols and derivatives thereof in the treatment of cancers and disorders involving excess cell proliferation. The general structures of the novel compounds of the present invention are shown in FIG. 1 and possible routes for their syntheses are provided in FIGS. 2–10. These molecules are in the class of compounds known as phenols or simple derivatives thereof.

The therapeutic use of the compounds of the present invention in treatment of cancers and other diseases and disorders involving excess cell proliferation is illustrated. The 5-hydroxyindoline derivatives were shown at various concentrations to inhibit the proliferation of human breast cancer cells (MDA MB 435 and MCF-7 breast cancer cells) and human promyelocytic leukemia cells (HL-60)) leukemia cells). The novel compounds of the present invention are strong inhibitors of cell growth. The novel features of these molecules include, inter alia, the nature of substituents on the phenolic ring and the fusion of a heteroatom-containing ring to it.

The novel compounds and methods of present invention may be used to treat either neoplastic diseases and non-neoplastic diseases. Representative examples of neoplastic diseases are ovarian cancer, bladder cancer, lung cancer, cervical cancer, breast cancer, prostate cancer, gliomas, fibrosarcomas, retinoblastomas, melanomas, soft tissue sarcomas, ostersarcomas, colon cancer, carcinoma of the kidney and pancreatic cancer.

Representative examples of non-neoplastic diseases are selected from the group consisting of psoriasis, benign proliferative skin diseases, ichthyosis, papilloma, basal cell carcinoma, squamous cell carcinoma, restinosis, scleroderma and hemangioma.

The methods of the present invention may be used to treat any animal. Most preferably, the methods of the present invention are useful in humans.

Generally, to achieve pharmacologically efficacious antiproliferative effects, the p-heteroatom-substituted phenols and analogs may be administered in any therapeutically effective dose. Preferably, the p-heteroatom-substituted phenols and analogs are administered in a dose of from about 1 mg/kg to about 10 mg/kg.

A wide variety of p-heteroatom-substituted phenols and their analogs are effective in the methods of the present invention. Representative examples of p-heteroatom-substituted phenols and their analogs are compounds such those selected from the group comprising of N-pivaloyl-5-hydroxy-3,4,6,7-tetramethylindole (27), 4,6-di-tert-butyl-2,3-dihydro-5-hydroxy-2(3H)-benzofuranone (24) 9-acetoxy-8,10-dimethyljulolidine (6), N-isobutyryl-5-acetoxy-3,4,6-trimethylindoline (12b) N-isobutyryl-5-methoxy-3,4,6-trimethylindoline (13), 5-hydroxy-2,4,6,7-tetramethylbenzo-furan (33) and N-isobutyryl-5-hydroxy-3,4,6-trimethylindoline (11b).

The term "individual" is meant to include animals and humans.

The term "biologically inhibiting" or "inhibition" of the growth of proliferating cells is meant to include partial or total growth inhibition and also is meant to include decreases in the rate of proliferation or growth of the cells. The biologically inhibitory dose of the composition of the present invention may be determined by assessing the effects of the test element on target malignant or abnormally proliferating cell growth in tissue culture, tumor growth in animals and cell culture or any other method known to those of ordinary skill in the art.

Administration of the compositions of the present invention may be by topical, intraocular, parenteral, oral, intranasal, intravenous, intramuscular, subcutaneous, or any other suitable means. The dosage administered is dependent upon the age, clinical stage and extent of the disease or genetic predisposition of the individual, location, weight, kind of concurrent treatment, if any, and nature of the pathological or malignant condition. The effective delivery system useful in the method of the present invention may be employed in such forms as capsules, tablets, liquid solutions, suspensions, or elixirs, for oral administration, or sterile liquid forms such as solutions, suspensions or emulsions. Any inert carrier is preferably used, such as saline, or phosphate-buffered saline, or any such carrier in which the novel compounds used in the method of the present invention have suitable solubility properties.

Preferably, delivery systems useful in the method of the present invention may be employed in such sterile liquid forms such as solutions, suspensions or emulsions. For topical use it may be employed in such forms as ointments, creams or sprays. Any inert carrier is preferably used, such as saline, or phosphate-buffered saline, or any such carrier in which the compounds used in the method of the present invention have suitable solubility properties.

There are a wide variety of pathological cancerous and noncancerous cell proliferative conditions for which the compositions and methods of the present invention will provide therapeutic benefits. These pathological conditions may occur in almost all cell types capable of abnormal cell proliferation. Among the cell types which exhibit pathological or abnormal growth are (1) fibroblasts, (2) vascular endothelial cells and (3) epithelial cells. It can be seen from the above that the method of the present invention is useful in treating local or disseminated pathological conditions in all or almost all organ and tissue systems of the individual.

It is specifically contemplated that pharmaceutical compositions may be prepared using the novel p-heteroatom-substituted phenols, and analogs thereof, of the present invention. In such a case, the pharmaceutical composition comprises the novel p-heteroatom-substituted phenols, or analogs thereof, of the present invention and a pharmaceutically acceptable carrier. A person having ordinary skill in this art would readily be able to determine, without undue experimentation, the appropriate dosages and routes of administration of the novel p-heteroatom-substituted phenols and analogs of the present invention.

In addition to the preferred antiproliferative activities of the novel p-heteroatom-substituted phenols and analogs of the present invention, these novel compounds also display novel cytoprotective, anti-mitogenic, angiostatic, anti-inflammatory, anti-atherosclerotic and anti-atherogenic activities. More preferably, the novel p-heteroatom-substituted phenols and analogs of the present invention are useful for various ocular reasons, e.g., aniostatic effects, inhibition of neovascularization, inhibition of cell proliferation following IOL implantation, inhibition of cataract formation (especially following vitrectomy) and heterodegenerative diseases, treatment for retinopathies, macular degeneration, photochemical injury, light damage injury (especially during ocular surgery).

The novel p-heteroatom-substituted phenols and analogs of the present invention may be used as part of an eye irrigating solution. Preferably, such an irrigating solution would have the following formulation: active agent: 0.01–1.0%; cremephor EL: 0.5%; sodium chloride: 0.64%; potassium chloride: 0.075%; calcium chloride: 0.048%; magnesium chloride: 0.03%; sodium acetate: 0.39%; sodium titrate: 0.17%; sodium hydroxide and/or hydrochloric acid: as necessary to adjust pH; and water for administration.

The novel p-heteroatom-substituted phenols and analogs of the present invention may be used as part of an topical ocular preparation. Preferably, such an topical preparation would have the following formulation: active agent: 1.0%; polyvinyl alcohol: 1.4%; monobasic sodium phosphate monohydrate: 0.05%; dibasic sodium phosphate (anhydrous) 0.15%; sodium chloride: 0.5%; disodium EDTA: 0.01%; polysorbate 80: 0.01%; benalkonium chloride solution: 0.01%; sodium hydroxide and/or hydrochloric acid: as necessary to adjust pH; and water for administration.

Furthermore, the present invention shows that p-heteroatom-substituted phenolic compounds function as anti-oxidants under both biological and non-biological screening protocols. As an example, assays of anti-oxidant activities using a protocol involving retinal pieces showed $IC_{50}$'s in the micromolar range.

The p-Heteroatom substituted phenolic compounds of the present invention possess antiproliferative properties, making them agents for prevention and treatment of proliferative diseases, including cancers of different cellular types and lineages.

Thus, the present invention is directed to an antiproliferative p-heteroatom-substituted phenol compound, or derivative thereof, having a structural formula selected from the group consisting of

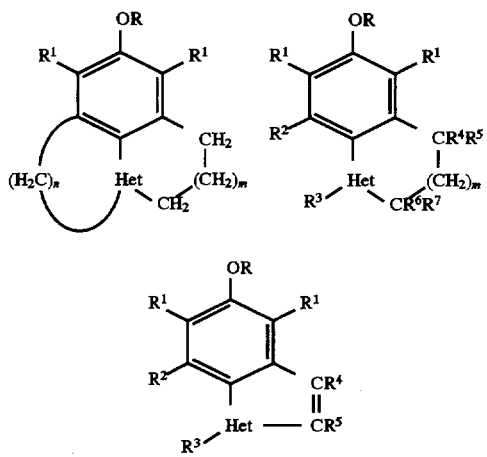

wherein m is 0 to 3, n is 0 when Het is oxygen or sulfur, 0 to 4 when Het is nitrogen, Het is nitrogen, oxygen or sulfur; wherein R is selected from the group consisting of hydrogen, alkyl, arylmethyl and acyl; $R^1$ is alkyl; $R^2$ is selected from the group consisting of hydrogen and alkyl; $R^3$ is selected from the group consisting of alkyl and acyl when Het is nitrogen,: (electron pair) when Het is oxygen or sulfur; $R^4$ is selected from the group consisting of hydrogen and alkyl; $R^5$ is selected from the group consisting of hydrogen and alkyl; and $R^6$ and $R^7$ are selected from the group consisting of hydrogen, alkyl and oxygen.

The following examples are given for the purpose of illustrating various embodiments of the invention and are not meant to limit the present invention in any fashion.

EXAMPLE 1

Synthesis of p-Heteroatom-substituted Phenols and Analogs Thereof

Melting points are uncorrected. Tetrahydrofuran was dried over benzophenone ketyl, toluene and methylene chloride were dried and distilled over calcium hydride. All air-sensitive and/or moisture-sensitive reactions were performed under a nitrogen or argon atmosphere. Concentration of solutions was by rotary evaporation unless otherwise noted.

IR spectra were obtained with a Nicolet 205 FT-IR spectrometer. Unless noted otherwise, $^1$H-NMR and $^{13}$C-NMR spectra were recorded with a GE QE-300 MHz spectrometer using tetramethylsilane as internal standard and $CDCl_3$ as solvent. HRMS data were obtained on a VG ZAB-E (Fisons) high-resolution mass spectrometer using the EI mode of ionization at 70 eV. Combustion analysis were performed by Atlantic Microlab Inc.

EXAMPLE 2

Synthesis of 2,6-Dimethylanisole (2)

Sodium hydroxide (20 g, 500 mmol) was dissolved in distilled water (200 mL) and placed in a round-bottom flask fitted with a reflux condenser. To the solution were added sequentially 2,6-dimethylphenol (1, 61 g, 500 mmol) and dimethyl sulfate (48 mL, 500 mmol). The mixture was heated at 60° C. for about 17 h, cooled, and transferred to a separatory funnel. The organic layer was separated, and the aqueous layer was extracted with benzene. The combined organic layers were washed sequentially with 10% aq. sodium hydroxide and brine, and dried ($MgSO_4$). Concentration of the solution gave 2,6-dimethylanisole (2, 39 g, 57% yield), bp 179°–182° C./750 torr (lit.: Burton, G. W.; Joyce, A.; Ingold, K. U. *Arch. Biochem. Biophys.*, 1982, 221, 281; 181° C.), as a colorless oil.

EXAMPLE 3

Synthesis of 2,6-Dimethyl-4-nitroanisole (3)

2,6-Dimethylanisole (2, 36 g, 260 mmol) was added dropwise over 0.5 h to stirred cold conc. nitric acid (200 mL) contained in round-bottom flask; stirring at room temperature was continued for 18 h. The mixture was poured onto crushed ice contained in a 1-L beaker. The resulting bright yellow solid was vacuum-filtered and dried. Recrystallization from ethanol-water gave 2,6-dimethyl-4-nitroanisole (3, 29 g, 62% yield) as a pale yellow solid, mp 90°–91° C. (lit.: Burton, G. W.; Joyce, A.; Ingold, K. U. *Arch. Biochem. Biophys.*, 1982, 221, 281; 89°–91° C.).

EXAMPLE 4

Synthesis of 4-Amino-2,6-dimethylanisole (4)

2,6-Dimethyl-4-nitroanisole (3, 29 g, 160 mmol), 10% Pd-C (200 mg) and ethanol (300 mL) were placed in a 500-mL Parr hydrogenation flask and hydrogenated at 50 psi for 24 h. The resulting solution was filtered through a silica gel column using ethyl acetate as eluent. Concentration of the solvent and drying under vacuum gave 23.7 g (98% yield) of 4-amino-2,6-dimethylanisole (4) as a brown-colored solid, mp 59°–60° C. (lit.: Bruice, T. C.; Kharasch, N.; Winzler, R. J. *J. Org. Chem.* 1953, 18, 83; 63° C.).

EXAMPLE 5

Synthesis of 9-Methoxy-8,10-dimethyljulolidine (5)

4-Amino-2,6-dimethylanisole (4, 1.4 g, 9.3 mmol), freshly distilled 1,3-bromochloropropane (13.7 mL, 139 mmol), anhydrous sodium carbonate (3.9 g, 37 mmol) and molecular sieves (4 Å, 1 g) were placed in a round-bottom flask and, under an argon atmosphere, stirred at 70° C. for 1 h, at 100° C. for 2 h and then heated under reflux for 17 h. The cooled reaction mixture was filtered and the filtrate was acidified with conc. hydrochloric acid. 1,3-Bromochloropropane was removed by steam distillation, and the residue was basified with aq. sodium hydroxide and extracted with ether. The combined extracts were washed with water and brine. Removal of solvents after drying ($MgSO_4$) gave a crude material which was purified by flash column chromatography, using 3:7 ethyl acetate:hexanes as eluent, to yield 9-methoxy-8,10-dimethyljulolidine (5, 1.2 g, 56% yield) as a yellow solid, mp 55°–57.5° C. Spectral data: $^1$H NMR: δ 2.0 (m, 4H), 2.12 (s, 6H), 2.63 (t, 4H, J=6.9 Hz), 3.0 (t, 4H, J=4.5 Hz) 3.61 (s, 3H); HRMS: calcd. for $C_{15}H_{21}NO$ 231.1623, fnd. 231.1618.

EXAMPLE 6

Synthesis of 9-Hydroxy-8,10-dimethyljulolidine hydrobromide

9-Methoxy-8,10-dimethyljulolidine (5, 109 mg, 0.5 mmol) and 49% hydrobromic acid (2 mL) were placed in a round-bottom flask and refluxed for 3 h under an argon atmosphere. The reaction mixture was cooled to room temperature and washed several times with water and then twice with acetone. Drying under vacuum gave julolidine hydrobromide (70 mg, 47% yield) as a colorless solid, mp 235°–237° C. Spectral data: $^1$H NMR ($CD_3OD$): δ 2.05 (s, 6H), 2.18 (q, 4H, J=6.8 Hz), 2.76 (t, 4H, J=6.6 Hz), 4.8 (s, 4H); $^{13}$C NMR ($CD_3OD$): δ 11.7, 18.7, 23.4, 51.7, 121.8, 125.0, 127.2, 152.0. Anal: calcd. for $C_{14}H_{20}BrNO$ C, 56.39, H, 6.76, N, 4.70, fnd. C, 56.09, H, 6.69, N, 4.67.

EXAMPLE 7

Synthesis of 9-Acetoxy-8,10-dimethyljulolidine (6)

9-Hydroxy-8,10-dimethyljulolidine hydrobromide (832 mg, 2.79 mmol) and methylene chloride (4 mL) were placed in a round-bottom flask and stirred under an argon atmosphere. Triethylamine (1.67 mL, 12 mmol) and acetic anhydride (0.55 mL, 5.8 mmol) were added sequentially, and the mixture was stirred at room temperature for about 16 h. The mixture was poured into water (15 mL) and extracted with methylene chloride. The combined methylene chloride extracts were washed sequentially with 5% hydrochloric acid and brine and dried ($Na_2SO_4$). Removal of solvents furnished a solid which was purified by flash column chromatography using 1:5 ethyl acetate:hexanes as eluent to yield 9-acetoxy-8,10-dimethyljulolidine (6, 680 mg, 94% yield), mp 112°–11° C. Spectral data: $^1$H NMR: δ 1.90 (s, 6H), 1.95 (m, 4H), 2.30 (s, 3H), 2.64 (t, 4H, J=7 Hz), 3.02 (t, 4H, J=5 Hz); $^{13}$C NMR: δ 12.3, 20.5, 22.3, 25.2, 50.0, 119.0, 125.3, 139.0, 142.0, 169.9. Anal: calcd. for $C_{16}H_{21}NO_2$ C, 74.10, H, 8.16, N, 5.41, fnd. C, 73.90, H, 8.20, N, 5.36.

EXAMPLE 8

Synthesis of 4-Acetamido-2,6-dimethylanisole (7)

4-Amino-2,6-dimethylanisole (4, 5 g, 33.2 mmol) was placed in a round-bottom flask fitted with a reflux condenser, and acetic anhydride (3.4 mL, 35.4 mmol) and acetic acid (3 mL, 53.1 mmol) were added sequentially. The mixture was heated to 50° C. for 4 h, cooled, poured into water and basified with saturated aq. sodium bicarbonate. The solution was extracted with methylene chloride, and the combined extracts were washed with brine and dried ($MgSO_4$). Removing the solvent and recrystallizing the resulting solid from hexane-methylene chloride yielded 4-acetamido-2,6-dimethylanisole (7, 5.3 g, 83% yield). Spectral data: $^1$H NMR: δ 2.1 (s, 3H), 2.2 (s, 6H), 3.65 (s, 3H), 7.10 (s, 2H), 8.10 (s, 1H); $^{13}$C NMR: δ 16.1, 24.2, 60.0, 121.5, 131.8, 134.3, 154.3, 169.8; CI-HRMS: calcd. for $C_{11}H_{16}NO_2$ (M+H$^+$) 194.1181, fnd. 194.1181.

EXAMPLE 9

Synthesis of 4-Acetamido-3-bromo-2,6-dimethylanisole

4-Acetamido-2,6-dimethylanisole (7, 8.6 g, 44.3 mmol) and acetic acid (30 mL) were placed in a round-bottom flask under an argon atmosphere. Bromine (2.7 mL, 44.3 mmol)

was added dropwise to the solution, after which the reaction mixture was stirred at room temperature for about 3 h, and then concentrated. The residue was diluted with methylene chloride and carefully washed sequentially with saturated aq. sodium bicarbonate and brine, and dried ($MgSO_4$). Removal of solvents gave a brown-colored solid which was recrystallized from methylene chloride-hexanes to yield 4-acetamido-3-bromo-2,6-dimethylanisole (10.3 g, 85% yield) as an off-white solid, mp 152°–153° C. Spectral data: $^1$H NMR: δ 2.18 (s, 3H), 2.24 (s, 3H), 2.35 (s, 3H), 3.66 (s, 3H), 7.55 (br s, 1H), 7.9 (s, 1H); $^{13}$C NMR: δ 16.1, 16.8, 24.6, 60.1, 114.5, 122.0, 130.5, 131.3, 131.5, 153.6, 168.1; CI-HRMS: calcd. for $C_{11}H_{15}BrNO_2$ (M+H$^+$) 272.0286, fnd. 272.0284.

EXAMPLE 10

Synthesis of N-Allyl-4-acetamido-3-bromo-2,6-dimethylanisole (8)

Sodium hydride (1.1 g, 27 mmol, 60% dispersion in oil) contained in a round-bottom flask fitted with a reflux condenser was washed using dry hexanes, tetrahydrofuran (50 mL) was added, and the suspension was stirred at 0° C. under a nitrogen atmosphere. A solution of 4-acetamido-3-bromo-2,6-dimethylanisole (7.3 g, 27 mmol) dissolved in tetrahydrofuran (50 mL) was added dropwise using a canulla over about 0.5 h. Allyl bromide (4.85 mL, 84.8 mmol) was added to the cold solution in one portion, and the mixture was warmed to 60° C. and held there for 17 h. The reaction mixture was quenched with saturated aq. ammonium chloride and extracted with diethyl ether. The combined extracts were washed with brine and dried ($MgSO_4$). Removal of solvents and purification of the resulting viscous liquid by flash column chromatography using 1:3 ethyl acetate:hexanes as eluent gave N-allyl-4-acetamido-3-bromo-2,6-dimethylanisole (8, 8.7 g, 85% yield) as a viscous liquid. Spectral data: $^{13}$C NMR: δ 15.2, 16.3, 21.5, 50.1, 59.3, 117.1, 123.3, 129.2, 130.2, 132.37, 132.4, 136.5, 156.2, 169.1; HRMS: calcd. for $C_{14}H_{19}BrNO_2$ (M+H$^+$) 312.0599, fnd. 312.0586.

EXAMPLE 11

Synthesis of N-Acetyl-5-methoxy-3,4,6-trimethylindoline (9)

A solution of N-allyl-4-acetamido-3-bromo-2,6-dimethylanisole (8, 1.1 g, 3.6 mmol) in dry toluene (237 mL) and tri-n-butylstannane (1.9 mL, 7.1 mmol) was placed in a round-bottom flask fitted with a reflux condenser and slowly warmed to 60° C. under a nitrogen atmosphere. A catalytic amount of azobisisobutyronitrile was added, and the resulting mixture was heated and stirred at 85° C. for 15 h. The cooled reaction mixture was washed sequentially with 1% aq. ammonia and brine, and dried ($MgSO_4$). Removal of solvents gave a liquid which was further purified by flash column chromatography using sequentially hexane and 1:3 ethyl acetate:hexanes as eluents to yield the indoline 9 (790 mg, 95% yield) as a colorless liquid. Spectral data: $^{13}$C NMR: δ 11.9, 16.4, 20.5, 23.9, 33.9, 57.3, 59.8, 116.5, 126.3, 129.7, 133.9, 137.6, 153.1, 168.2; HRMS: calcd. for $C_{14}H_{20}NO_2$ (M+H$^+$) 234.1494, fnd. 234.1487.

EXAMPLE 12

Synthesis of N-Acetyl-5-hydroxy-3,4,6-trimethylindoline (11a)

Boron tribromide (1.4 mL of 1M solution in methylene chloride, 1.4 mmol) was added to a cooled (−78° C.) solution of indoline 9 (110 mg, 47 mmol) dissolved in methylene chloride (2 mL). The resulting solution was maintained at −78° C. (1 h), then slowly warmed to room temperature and held there for 17 h. The cooled reaction mixture was quenched with a few drops of methanol followed by cold water. The solution was extracted with methylene chloride and the combined organic layers were washed with brine and dried ($MgSO_4$). Removal of solvents gave a solid, which was recrystallized from methylene chloride-hexanes to afford the indoline 11a (95 mg, 92% yield) as a colorless solid, mp 204°–205° C. Spectral data: $^{13}$C NMR ($CD_3SOCD_3$): δ 12.3, 17.2, 20.7, 23.7, 33.4, 56.4, 115.3, 120.7, 122.6, 133.9, 134.3, 149.1, 167.4; HRMS: calcd. for $C_{13}H_{17}NO_2$ 219.1259, fnd. 219.1261. Anal: calcd. for $C_{13}H_{17}NO_2C$, 71.21, H, 7.81, N, 6.39, fnd. C, 71.06,H, 7.84, N, 6.33.

EXAMPLE 13

Synthesis of N-Acetyl-5-acetoxy-3,4,6-trimethylindoline (12a)

To an ice-cold solution of indoline 11a (219 mg, 1 mmol) dissolved in methylene chloride (5 mL) were added sequentially pyridine (1 mL) and acetic anhydride (0.12 mL, 1.1 mmol), and the resulting mixture was stirred over a range of 0° C. to room temperature for 18 h. The reaction mixture was quenched with water and extracted with methylene chloride. The combined organic extracts were washed with 5% aq. hydrochloric acid and brine then dried ($MgSO_4$). Removal of solvents and chromatographic purification of the residue using 3:7 ethyl acetate:hexanes as eluent gave the acetate 12a (228 mg, 87% yield) as a pale yellow solid. This was recrystallized from hexanes-methylene chloride to afford a colorless solid, mp 128°–130° C. Spectral data: $^1$H NMR: δ 1.23 (d, 3H, J=7 Hz), 2.04 (s, 3H), 2.10 (s, 3H), 2.17 (s, 3H), 2.31 (s, 3H), 3.61 (dd, 1H, J=10.2, 2.3 Hz), 4.13 (t, 1H, J=9.53 Hz), 7.96 (s, 1H); $^{13}$C NMR: δ 12.3, 16.7, 20.4, 20.7, 24.8, 33.9, 57.4, 116.4, 125.7, 129.3, 133.7, 139.5, 144.2, 168.5, 169.1; HRMS: calcd. for $C_{15}H_{20}NO_3$ (M+H$^+$) 262.1443, fnd. 262.1446.

EXAMPLE 14

Synthesis of 5-Methoxy-3,4,6-trimethylindoline

To an ice-cold solution of indoline 9 (377 mg, 1.6 mmol) dissolved in tetrahydrofuran (5 mL) and kept under an argon atmosphere was added lithium triethylborohydride (3.2 mL, 3.2 mmol), and the mixture was stirred over the range of 0° C. to room temperature for 20 h. The reaction mixture was quenched with 3N hydrochloric acid, and volatiles were removed under vacuum. The resulting solution was acidified to pH 2 with additional 3N hydrochloric acid and washed with methylene chloride. The aqueous solution was basified with saturated aq. sodium bicarbonate and extracted with methylene chloride. The organic extracts were washed with brine and dried ($MgSO_4$). Removal of solvents gave crude methoxyindoline (200 mg, 65% yield) as a brownish yellow oil, which was used without further purification.

EXAMPLE 15

Synthesis of 5-Hydroxy-3,4,6-trimethylindoline (10)

The methoxyindoline (185 mg, 0.96 mmol) and 49% hydrobromic acid (4 mL) were placed in a round-bottom flask fitted with a reflux condenser and heated to 100° C. for 3 h under a nitrogen atmosphere. The solution was cooled, diluted with water, and washed off with ether. The acidic solution was basified with saturated aq. sodium bicarbonate and extracted with methylene chloride. The combined organic extracts were washed with brine and dried (MgSO$_4$). Removal of solvents gave a brown-colored oil which was purified by filtration through a silica gel plug using 1:1 ethyl acetate:hexanes as eluent to afford indoline 10 (160 mg, 94% yield) as a yellow oil. This material was immediately used in the next step.

EXAMPLE 16

Synthesis of N-Isobutyryl-5-hydroxy-3,4,6-trimethylindoline (11b)

To an ice-cold solution of indoline 10 (160 mg, 0.9 mmol) dissolved in methylene chloride (4 mL) and kept under an argon atmosphere were added sequentially pyridine (1 mL) and isobutyryl chloride (0.1 mL, 9 mmol); the mixture was stirred over the range of 0° C. to room temperature for some 17 h. The mixture was diluted with methylene chloride, washed with brine and dried (MgSO$_4$). Removal of solvents followed by purification of the residue using 1:9 ethyl acetate:hexanes as eluent afforded the desired N-isobutyryl-5-hydroxy-3,4,6-trimethylindoline (11b, 163 mg, 73% yield) as a colorless solid, mp 123°–125° C. Spectral data: $^1$H NMR: δ1.1–1.25 (m, 9H), 2.17 (s, 3H), 2.20 (s, 3H), 2.72 (quintet, 1H, J=6.5 Hz), 3.35 (t, 1H, J=6.5 Hz), 3.78 (dd, 1H, J=10.1, 1.0 Hz), 4.13 (t, 1H, J=9.1 Hz), 7.95 (s, 1H); $^{13}$C NMR: δ 11.9, 16.5, 18.8, 19.3, 20.7, 33.1, 34.0, 56.3, 116.8, 119.5, 122.1, 134.1, 135.0, 148.8, 175.0; HRMS: calcd. for C$_{15}$H$_{21}$NO$_2$ 247.1523, fnd. 247.1573. Anal: calcd. for C$_{15}$H$_{21}$NO$_2$ C, 72.85, H, 8.55, N, 5.66, fnd. C, 72.63, H, 8.59, N, 5.60.

EXAMPLE 17

Synthesis of N-Isobutyryl-5-acetoxy-3,4,6-trimethylindoline (12b).

To an ice-cold solution of N-isobutyryl-5-hydroxy-3,4,6-trimethylindoline (11b, 49 mg, 0.2 mmol) dissolved in methylene chloride (2 mL) were added sequentially pyridine (0.16 mL, 2 mmol) and acetic anhydride (0.1 mL, 1 mmol). The mixture was stirred over the range of 0° C. to room temperature for 17 h. The mixture was diluted with methylene chloride, transferred to a separatory funnel and washed sequentially with 10% hydrochloric acid, saturated aq. sodium bicarbonate and brine. Removal of solvents after drying (MgSO$_4$) gave a viscous liquid, which was purified by flash column chromatography, using 1:4 ethyl acetate:hexanes as eluent, to afford the N-isobutyryl-5-acetoxy-3,4,6-trimethylindoline (12b, 45 mg, 77% yield) as a colorless solid, mp 118°–120° C. Spectral data: $^1$H NMR: δ 2.0 (s, 3H), 2.06 (s, 3H), 2.26 (s, 3H), 2.7 (quintet, 1H, J=6.7 Hz), 3.3 (t, 1H, J=6.7 Hz), 3.7 (dd, 1H, J=10.2, 1.2 Hz), 4.1 (t, 1H, J=9.3 Hz), 8.0 (s, 1H); CI-HRMS: calcd. for C$_{17}$H$_{24}$NO$_3$ (M+H$^+$) 290.1756, fnd. 290.1756.

EXAMPLE 18

Synthesis of N-Isobutyryl-5-methoxy-3,4,6-trimethylindoline (13)

Sodium hydride (7 mg, 0.18 mmol) contained in a round-bottom flask was washed using dry hexanes and tetrahydrofuran (2 mL) was added, and the suspension was stirred at 0° C. under nitrogen atmosphere. A solution of N-isobutyryl-5-hydroxy-3,4,6-trimethylindoline (11 b, 42 mg 0.17 mmol) dissolved in tetrahydrofuran (2 mL) was added dropwise using a syringe. Methyl iodide (0.2 mL) was added to the cold solution in one portion, and the mixture was heated under reflux for 17 h. The reaction mixture was cooled, quenched with saturated aq. ammonium chloride solution and extracted with ether. The combined extracts were washed with brine and dried (MgSO$_4$). Removal of solvents gave a viscous liquid which was purified by flash column chromatography using 1:4 ethyl acetate:hexanes as eluent, to afford N-isobutyryl-5-methoxy-3,4,6-trimethylindoline (13, 40 mg, 90% yield) as a viscous liquid. Spectral data: $^1$H NMR: δ 1.20–1.35 (m, 9H), 2.22 (s, 3H), 2.27 (s, 3H), 2.74 (quintet, 1H, J=6.5 Hz), 3.30 (t, 1H, J=6.5 Hz), 3.65 (s, 3H), 3.76 (dd, 1H, J=10, 1 Hz), 4.15 (t, 1H, J=9 Hz), 8.0 (s, 1H).

EXAMPLE 19

Synthesis of N-Pivaloyl-5-hydroxy-3,4,6-trimethylindoline (11c)

Treatment of indoline 10 (160 mg, 0.9 mmol) according to a procedure similar to one used for preparing 11b, with substitution of pivaloyl chloride for isobutyryl chloride, afforded 11c (176 mg, 75% yield) as a colorless solid, mp 144°–145° C. Spectral data: $^{13}$C NMR: δ 11.7, 16.4, 19.5, 27.6, 39.9, 57.4, 117.9, 119.2, 121.9, 133.7, 136.0, 148.8, 176.0; HRMS: calcd. for C$_{16}$H$_{23}$NO$_2$ 261.1229, fnd. 261.1921. Anal: calcd. for C$_{16}$H$_{23}$NO$_2$ C, 73.53, H, 8.87, N, 5.36, fnd. C, 73.60, H, 8.91, N, 5.36.

EXAMPLE 20

Synthesis of N-(2-Methyl-2-propenyl)-4-acetamido-3-bromo-2,6-dimethylanisole (14)

Treatment of 4-acetamido-3-bromo-2,6-dimethylanisole (2.7 g, 10 mmol) according to a procedure similar to the one used for making compound 8, substituting methallylbromide for allyl bromide, afforded 14 (2.8 g, 86% yield) as a viscous liquid. Spectral data: $^1$H NMR (250 MHz): δ 1.71 (s, 3H), 1.75 (s, 3H), 2.18 (s, 3H), 2.33 (s, 3H), 3.26 (d, 1H, J=15 Hz), 3.66 (s, 3H), 4.62 (s, 1H), 4.75 (s, 1H), 4.82 (d, 1H, J=15 Hz), 6.82 (s, 1H).

EXAMPLE 21

General Procedure for palladium-catalyzed Cyclization of Bromoanilides to Produce Indoles and Indolines Palladium (II) acetate (0.1 eq.), triphenylphosphine (0.2 eq.), tetraethylammonium chloride (1 eq.), sodium formate (1.1 eq.) and dimethyl formamide were placed in a round-bottom flask fitted with a reflux condenser, and the mixture was stirred under a nitrogen atmosphere. A solution of anilide dissolved in dimethyl formamide was added, and the mixture was heated at either 85° or 100° C. for several hours, until TLC analysis showed consumption of all precursor. The mixture was cooled, gravity-filtered and the filter cake was washed with diethyl ether. Concentration followed by distillation of the dimethyl formamide under vacuum gave a viscous liquid, which was purified by flash column chromatography

EXAMPLE 22

Synthesis of N-Acetyl-5-methoxy-3,3,4,6-tetramethylindoline (15)

Treatment of 14 (1.9 g, 5.8 mmol) according to the general procedure used for Pd-catalyzed cyclization afforded 15 (1.2 g, 85% yield) as a viscous liquid. $^{13}$C NMR: δ 11.6, 16.4, 24.1, 26.9, 41.1, 59.9, 64.7, 116.7, 126.5, 129.7, 135.7, 137.8, 153.4, 168.0; HRMS: calcd. for $C_{15}H_{21}NO_2$ 247.1572, fnd. 247.1581.

EXAMPLE 23

Synthesis of N-Acetyl-5-hydroxy-3,3,4,6-tetramethylindoline (16)

Treatment of 15 (741 mg, 3 mmol) according to a procedure similar that used for making 11a afforded 16 (524 mg, 75% yield) as a colorless solid, mp 173°–174° C. Spectral data: $^{13}$C NMR (CD$_3$SOCD$_3$): δ 11.7, 17.3, 23.9, 27.0, 40.6, 63.7, 115.4, 121.1, 122.8, 135.6, 149.2, 167.2; HRMS: calcd. for $C_{14}H_{19}NO_2$ 233.1415, fnd. 233.1416. Anal: calcd. for $C_{14}H_{19}NO_2$ C, 72.08, N, 6.00, H, 8.20, fnd. C, 71.88, N, 5.95, H, 8.22.

EXAMPLE 24

Synthesis of N-Pivaloyl-4-amino-2,6-dimethylanisole

Into an ice-cold solution of aniline 4 (15.1 g, 100 mmol) dissolved in methylene chloride (100 mL) were added sequentially pyridine (17.5 mL) and pivaloyl chloride (12.3 mL, 100 mmol) dropwise, and the resulting mixture was stirred at room temperature for 15 h. The mixture was diluted with methylene chloride and washed sequentially with 10% aq. hydrochloric acid, saturated aq. sodium bicarbonate and brine. Removal of solvents after drying (MgSO$_4$) gave the pivalamide (19.8 g, 86% yield) as a pale brown solid, mp 126°–128° C. Spectral data: $^1$H NMR: δ 1.30 (s, 9H), 2.23 (s, 6H), 3.68 (s, 3H), 7.18 (s, 2H).

EXAMPLE 25

Synthesis of N-Pivaloyl-4-amino-3-bromo-2,6-dimethylanisole (17)

Into an ice-cold solution of the pivalanilide (19.8 g, 85.7 mmol) dissolved in acetic acid (100 mL) was added bromine (4.4 mL, 85.7 mmol) dropwise using a syringe, and the resulting solution was stirred at room temperature for 19 h. The mixture was diluted with methylene chloride, transferred to a beaker and carefully basified with saturated aq. sodium bicarbonate. The biphasic solution was transferred to a separatory funnel and extracted with methylene chloride. The combined methylene chloride layers were dried (MgSO$_4$) and concentrated to give a brown-colored solid which was recrystallized from methylene chloride-hexane to afford 119 (23.5 g, 87% yield) as a pale brown solid, mp 87°–88° C. Spectral data: $^1$H NMR: a 1.32 (s, 9H), 2.22 (s, 3H), 2.36 (s, 3H), 3.65 (s, 3H), 7.90 (br s, 1H), 8.05 (s, 1H).

EXAMPLE 26

Synthesis of N-(2-Methyl-2-propenyl), N-Pivaloyl-4-amino-3-bromo-2,6-dimethylanisole (18)

Sodium hydride (1.5 g, 38.3 mmol) contained in a round-bottom flask fitted with a reflux condenser was washed using dry hexanes, tetrahydrofuran (50 mL) was added and the suspension was stirred at 0° C. under a nitrogen atmosphere. A solution of compound 119 (12 g, 38.3 mmol) dissolved in tetrahydrofuran (70 mL) was added by a cannula over 0.5 h. Methallyl bromide (6 mL, 59.5 mmol) was added dropwise using a syringe, and the mixture was slowly heated to 60° C. Stirring and heating were continued for 18 h. The mixture was quenched with saturated aq. ammonium chloride and extracted with ether. The combined ethereal layers were washed with brine and dried (MgSO$_4$). Removal of the solvents and purification of the residue by filtering through a small silica gel column using 1:3 ethyl acetate-hexane as the eluent gave 18 (13 g, 93% yield) as a pale yellow liquid. Spectral data: $^1$H NMR: δ 1.00 (s, 9H), 1.70 (s, 3H), 2.21 (s, 3H), 2.34 (s, 3H), 3.39 (d, 1H, J=13 Hz), 3.68 (s, 3H), 4.65 (br s, 1H), 4.77 (br s, 1H), 4.99 (d, 1H, J=15.2 Hz), 6.93 (s, 1H); $^{13}$C NMR: δ 16.0, 17.1, 20.7, 28.8, 41.0, 56.8, 60.2, 112.0, 125.6, 129.8, 130.7, 133.0, 138.3, 140.8, 156.8, 177.3; HRMS: calcd. for $C_{18}H_{27}BrNO_2$ (M+H$^+$) 368.1225, fnd. 368.1213.

EXAMPLE 27

Synthesis of N-Pivaloyl-3,3,4,6-tetramethyl-5-methoxyindoline (19)

Treatment of 18 (5.1 g, 14 mmol) according to the general procedure used for Pd-catalyzed cyclization afforded 19 (2.1 g, 52% yield) as a colorless solid, mp 103°–104° C. Spectral data: $^1$H NMR: δ 1.32 (s, 9H), 1.38 (s, 6H), 2.30 (s, 3H), 2.33 (s, 3H), 3.65 (s, 3H), 3.85 (s, 2H), 7.95 (s, 1H); $^{13}$C NMR: δ 11.5, 16.5, 25.8, 27.6, 39.9, 41.8, 59.9, 64.6, 118.3, 126.2, 129.4, 135.7, 139.4, 153.4, 175.9.

EXAMPLE 28

Synthesis of 5-Hydroxy-3,3,4,6-tetramethylindoline hydrobromide

In a round-bottom flask fitted with a reflux condenser were placed 19 (6 g, 20.8 mmol) and 49% hydrobromic acid (100 mL), and the mixture was heated at 100° C. for 18 h under a nitrogen atmosphere, and then cooled. The hydrobromic acid was removed under reduced pressure, and the resulting solid was washed with hexanes to yield 5-hydroxy-3,3,4,6-tetramethylindoline hydrobromide (5.2 g, 92% yield) as a colorless solid. Spectral data: $^1$H NMR (CD$_3$OD): δ 1.50 (s, 6H), 2.25 (s, 3H), 2.30 (s, 3H), 3.50 (s, 2H), 7.00 (s, 1H); $^{13}$C NMR (CD$_3$OD): δ 12.0, 17.1, 26.6, 44.6, 59.9, 119.2, 123.2, 126.7, 127.1, 140.6, 156.2.

EXAMPLE 29

Synthesis of N-Pivaloyl-5-hydroxy-3,3,4,6-tetramethylindoline (20)

Treatment of 5-hydroxy-3,3,4,6-tetramethylindoline hydrobromide (218 mg, 0.8 mmol) according to a procedure similar to that used for making N-isobutyryl-5-hydroxy-3,4,6-trimethylindoline (11b) afforded 20 (155 mg, 70% yield) as a colorless solid, mp 143°–144° C. Spectral data: $^{13}$C NMR: δ 11.3, 16.4, 26.1, 27.7, 39.9, 41.9, 64.6, 118.1, 119.3, 121.3, 135.9, 136.7, 148.9, 175.6; CI-HRMS: calcd. for $C_{17}H_{26}NO_2$ (M+H$^+$) 276.1964, fnd. 276.1955. Anal: calcd. for $C_{17}H_{25}NO_2$ C, 74.15, H, 9.15, N, 5.09, fnd. C, 73.94, H, 9.21, N, 5.04.

EXAMPLE 30

Synthesis of 2,6-Di-tert-butyl-1,4-hydroquinone.

2,6-Di-tert-butyl-1,4-benzoquinone (5.0 g, 22.6 mmol), prepared according to the method of Minisu, et al., *J. Org. Chem.*, 54:728,(1989) was dissolved in diethyl ether (40 mL) and shaken vigorously in a separatory funnel with a solution of sodium dithionite (8 g, 33 mmol) in water (60 mL). The color of the organic layer changed from bright mustard to brown and finally to pale yellow. This layer was washed with brine and dried ($Na_2SO_4$). Concentration afforded 4.6 g (92% yield) of a peach-colored solid, mp 103°–106° C. Spectral data: $^1$H NMR: δ 1.45 (s, 18H), 4.80 (br s, 1H), 5.45 (br s, 1H), 6.20 (s, 2H); $^{13}$C NMR: δ 30.13, 34.34, 111.97, 137.49, 147.62, 147.90.

EXAMPLE 31

Synthesis of -Allyloxy-1,3-di-tert-butylphenol

A solution of 2,6-di-tert-butyl-1,4-hydroquinone (5.8 g, 26 mmol) in tetrahydrofuran (50 mL) was added dropwise to a suspension of sodium hydride in tetrahydrofuran at 0° C. This mixture was stirred for 15 min and then allyl bromide (3.47 g, 27.7 mmol) was added dropwise over 3–5 min. The solution was allowed to warm to room temperature and left stirring for 16 h. It was then quenched with ice water, extracted into diethyl ether, washed with brine and dried ($Na_2SO_4$). Concentration afforded a crude dark oil which was purified by flash column chromatography over silica gel using a solvent system of hexanes and ethyl acetate (95/5, $R_f$=0.42) and resulted in 4.40 g of a yellow liquid (64% yield). Spectral data: $^1$H NMR: δ 1.42 (s, 18H), 4.44 (d, 2H, J=5.7 Hz), 4.78 (br s, 1H), 5.28 (d, 1H, J=10.3 Hz), 5.42 (d, 1H, J=16.2 Hz), 6.02–6.16 (m, 1H), 6.78 (s, 2H); $^{13}$C NMR: δ 30.20, 34.57, 69.54, 111.56, 117.38, 134.07, 137.15, 147.84, 151.57.

EXAMPLE 32

Synthesis of 5-Allyloxy-1,3-di-tert-butyl-2-trimethylsiloxybenzene (21).

5-Allyloxy-1,3-di-tert-butylphenol (0.03 mmol) and bistrimethylsilylacetamide (BSA, 15.5 g, 0.076 mol) were dissolved in dry acetonitrile (30 mL) The resulting solution was refluxed for 24 h and then poured into a beaker containing ice water (50 mL). The solution was extracted with diethyl ether (3×20 mL), washed with brine and dried ($Na_2SO_4$). Concentration afforded 10.2 g of a tawny brown liquid. This crude material was rapidly passed through a 5 cm-long pad of silica gel (90-mm diameter) with 5% ethyl acetate in hexanes to yield 8.4 g of liquid product. Spectral data: $^1$H NMR: δ 0.40 (s, 9H), 1.40 (s, 18H), 4.48 (d, 2H), 5.28 (dd, 1H), 5.42 (dd, 1H), 6.02–6.16 (m, 1H), 6.84 (s, 2H).

EXAMPLE 33

Synthesis of 2-Allyl-3,5-di-tert-butyl-4-trimethylsiloxyphenol (22a)

Phenol 22 was prepared by $BCl_3$-assisted rearrangement of 5-allyloxy-1,3-di-tert-butyl-2-trimethylsiloxybenzene (21) according to Gilbert and Pinto, *J. Org. Chem.* 1992, 57, 5271, for the preparation of 2-allyl-3,5,6-trimethyl-1,4-hydroquinone, with the following modifications: the ratio of substrate to $BCl_3$ was 1:1.1 and the reaction was quenched at −70° C. by the addition of a saturated aqueous solution of sodium carbonate and by allowing the resulting mixture to reach ambient temperatures. The crude product was isolated as a viscous green oil (81% yield) and acetylated without further purification. Spectral data: $^1$H NMR: δ 0.18 (s, 9H), 1.34 (s, 9H), 1.53 (s, 9H), 3.63 (d, 2H, J=5.2 Hz), 5.10 (dd, 1H, J=17.3, 2 Hz), 5.20 (dd, 1H, J=10.2, 2 Hz), 5.92–6.08 (m, 1H), 6.68 (s, 1H).

EXAMPLE 34

Synthesis of 1-Acetoxy-2-allyl-3,5-di-tert-butyl-4-trimethylsiloxybenzene (22b)

Compound 22b was prepared by the acetylation of 2-allyl-3,5-di-tert-butyl-4-trimethylsiloxyphenol (22a) according to the method of Gilbert and Pinto, *J. Org. Chem.* 1992, 57, 5271–5276. Spectral data: $^1$H NMR: δ 0.18 (s, 9H), 1.36 (s, 9H), 1.23 (s, 9H), 2.21 (s, 2H), 3.55 (d, 2H), 4.90 (dd, 1H), 4.98 (dd, 1H), 5.77–5.90 (m, 1H), 6.78 (s, 1H); EI-MS: m/z 376 ($M^+$), 334 (base, $M^+$-$CH_2CO$), 319, 73, 57; HRMS: Calcd. for $C_{22}H_{36}O_3Si$ 376.2434, fnd. 376.2430.

EXAMPLE 35

Synthesis of 6'-Acetoxy-2'-4'-di-tert-butyl-3'-trimethylsiloxyphenylacetaldehyde (23a)

Ozonolysis of 22b according to the procedure of Gilbert and Pinto, *J. Org. Chem.* 1992, 57, 5271, for the ozonolysis of 2-allyl-1,4-diacetoxy-3,5,6-trimethylbenzene afforded 23a, which was obtained as a white solid (50% yield) after flash column chromatography over silica gel (Skellysolve B-ethyl acetate, 90:10, $R_f$=0.23). Spectral data: $^1$H NMR: δ 0.22 (s, 9H), 1.37 (s, 9H), 1.44 (s, 9H), 2.20 (s, 2H), 3.74 (d, 2H, J=1.6 Hz), 6.88 (s, 1H), 9.52 (t, 1H, J=1.7 Hz); HRMS: calcd. for $C_{21}H_{34}SiO_4$ 378.2226, fnd. 378.2214.

EXAMPLE 36

Synthesis of 6'-Acetoxy-2'-4'-di-tert-butyl-3'-trimethylsiloxyphenylacetic acid (23b)

Aldehyde 23a was oxidized to 23b according to the procedure of Gilbert and Pinto, *J. Org. Chem.* 1992, 57, 5271. The acid was obtained as a white solid (88% yield). Spectral data: $^1$H NMR: δ 0.20 (s, 9H), 1.35 (s, 9H), 1.45 (s, 9H). 2.23 (s, 3H), 3.80 (s, 2H), 6.90 (s, 1H), carboxylic acid proton was not detected. EI MS: m/z 394 ($M^+$, very low intensity), 352 ($M^+$-$CH_2CO$), 334 (base, 352-$H_2O$), 319, 291,263, 73, 57, 45.

EXAMPLE 37

Synthesis of 4,6-Di-tert-butyl-2,3-dihydro-5-hydroxy-2(3H)-benzofuranone (24).

With rigorous exclusion of oxygen from the reaction vessel, a solution of 23b (2.30 g, 5.8 mmol) in methanol (15 mL) was sparged with argon for 20 min. Potassium carbonate (0.80 g, 5.8 mmol) was added and the resulting mixture was allowed to stir for 3 hours, after which time the pH of the reaction mixture was brought to 3 (pHydrion paper) by addition of 10% hydrochloric acid solution. The mixture was dissolved in 20 mL diethyl ether/water (1:1) and the organic layer was separated and sequentially washed with water and brine and then dried ($Na_2SO_4$). Concentration afforded 2.03 g of an orange-red oil. The crude material was purified by flash column chromatography over silica gel using a solvent system of hexanes and ethyl acetate (90:10, $R_f$=0.23). The yellow solid thus obtained was recrystallized from hexanes to afford a cream-colored, amorphous solid, mp 102°–104° C. Spectral data: IR (Nujol) 3461, 1773 $cm^{-1}$; $^1$H NMR: δ 1.45 (s, 3H), 1.55 (s. 3H), 3.95 (s. 2H), 5.10 (s, 1H), 6.95 (s, 1H); $^{13}$C NMR: δ 30.10, 31.13, 34.49, 36.81, 107.50, 118.41, 133.69, 137.14, 148.77, 150.68, 174.82; HRMS: calcd. for $C_{16}H_{22}O_3$ 262.1569, fnd. 262.1570. Anal.: calcd. for $C_{16}H_{22}O_3$ C, 73.25, H, 8.45, fnd. C, 73.00, H, 8.40.

EXAMPLE 38

Synthesis of 2,3,5-Trimethyl-1,4-benzoquinone-1-mono-oxime

To a solution of 2,3,5-trimethyl-1,4-benzoquinone (70 g, 0.51 mol) of hot ethanol (200 mL) was added a warm solution of hydroxylamine hydrochloride (35 g, 0.50 mol) and conc. hydrochloric acid (5 mL) in water (100 mL). The resulting red solution was stirred for 10 min at 60° C., stoppered and allowed to cool overnight in a refrigerator. The bright yellow precipitate was collected by vacuum filtration and dried to yield 63.9 g (83% yield) of crude product. Recrystallization from 50% aq. ethanol afforded the product as a yellow solid, mp 175° C. (dec.) (lit.: Smith, L. I.; Schubert, W. M. *J. Am. Chem. Soc.* 1948, 70, 2656; mp 182° C.). Spectral data: $^1$H NMR (CD$_3$SOCD$_3$): δ 1.90 (s, 3H), 1.93 (s, 3H), 2.30 (s, 3H), 7.55 (s, 1H), 12.95 (s, 1H, exchangeable with D$_2$O); $^{13}$C NMR (CD$_3$COCD$_3$): δ 11.49, 12.94, 16.09, 120.53, 132.77, 137.39, 140.72, 149.04, 186.13.

EXAMPLE 39

Synthesis of 4-Hydroxy-2,3,5-trimethylaniline (25a)

The method of Smith and Schubert, *J. Am. Chem. Soc.* 1948, 70, 2656, was followed. 2,3,5-Trimethyl-1,4-benzoquinone-1-mono-oxime (50 g, 0.30 mol) was dissolved in aq. sodium hydroxide solution (49.5 g, 1.24 mol of NaOH in 720 mL of water). The resulting intense red solution was cooled in an ice bath and stirred while sodium dithionite (126.1 g, 0.73 mol) was added. The red color faded and a beige precipitate formed. The mixture was stirred for 2 hours and allowed to come to ambient temperature. It was then cooled in ice and filtered. The crude 25a was pressed dry, rapidly transferred to an evacuated atmosphere and dried further (50° C./0.3 torr, 24 hours), mp 130°–131° C. with dec. (lit.: Smith, L. I.; Schubert, W. M. *J. Am. Chem. Soc.* 1948, 70, 2656; 132°–134° C. dec.). Spectral data: $^1$H NMR (CD$_3$SOCD$_3$): δ 1.90 (s, 3H), 2.05 (2s, 3H each), 4.10 (br s, 2H), 6.25 (s, 1H), 7.10 (br s, 1H); $^{13}$C NMR (CD$_3$SOCD$_3$): δ 12.88, 13.25, 16.78, 114.39, 118.43, 122.25, 123.95, 138.81, 144.11.

EXAMPLE 41

Synthesis of 4-Hydroxy-2,3,5-trimethylpivalanilide (25b)

A solution of 4-hydroxy-2,3,5-trimethylaniline (99.2 g, 0.66 mol), pivaloyl chloride (87.1 g, 0.72 mol) and pyridine (1.4 L) was stirred for 16 hours under argon. The reaction mixture was poured onto ice and extracted into diethyl ether. The organic layer was sequentially washed with 10% hydrochloric acid, aq. sodium bicarbonate solution, water and brine. Drying and concentration afforded a purple solid. This solid was washed repeatedly with a solvent mixture of ethyl acetate and hexanes (3:7) to yield 91 g (59% yield) of the desired compound as a brown solid. Spectral data: IR (Nujol) 3410, 3250, 1652 cm$^{-1}$; $^1$H NMR (CD$_3$SOCD$_3$): δ1.35 (s, 1H), 2.10 (s, 3H), 2.15 (s, 3H), 2.20 (s, 3H), 5.35 (br s, 1H), 6.95 (s, 1H), 7.10 (br s, 1H).

EXAMPLE 42

Synthesis of 4-Acetoxy-2,3,5-trimethylpivalanilide (25c).

A solution of 25b (50.5 g, 0.21 mol), acetic anhydride (30 mL), triethylamine (59 mL) and dry dichloromethane (370 mL) was stirred for 14 hours. The reaction mixture was concentrated, and the residual brown solid was washed with water and diethyl ether and dried (oil pump) to yield 54.9 g (93% yield) of 25c as a cream-colored solid. Spectral data: IR (Nujol) 3340, 1764, 1644 cm$^{-1}$; $^1$H NMR (CD$_3$SOCD$_3$): δ 1.25 (s, 9H), 2.00 (s, 6H), 2.05 (s, 3H), 2.35 (s, 3H), 6.85 (s, 1H), 8.90 (s, 1H); $^{13}$C NMR (CD$_3$SOCD$_3$): δ 3.01, 4.25, 5.07, 10.20, 17.41, 116.54, 116.75, 118.61, 121.89, 123.88, 135.62, 156.65, 160.45.

EXAMPLE 43

Synthesis of 4-Acetoxy-6-bromo-2,3,5-trimethylpivalanilide (25d).

A solution of 25c (5 g, 18 mmol), bromine (1.85 mL, 36 mmol) and iodine (1.24 g, 4.9 mmol) in glacial acetic acid (65 mL) was heated between 65°–73° C. for 1 hour. The acetic acid was distilled (40° C./0.3 torr) and the red viscous residue, taken up in 75 mL of 1:1 CH$_2$Cl$_2$/hexanes, was washed with water, brine and dried (Na$_2$SO$_4$). Concentration afforded a quantitative yield of 25d as an off-white solid. Spectral data: $^1$H NMR (CD$_3$SOCD$_3$): δ 1.25 (s, 9H), 2.00 (s, 3H), 2.10 (s, 3H), 2.25 (s. 3H), 2.45 (s, 3H), 9.15 (s, 1H); $^{13}$C NMR (CD$_3$SOCD$_3$): δ 3.21, 5.30, 7.27, 10.19, 11.03, 17.34, 133.81, 117.62, 118.37, 123.51, 125.31, 136.25, 158.61, 165.96.

EXAMPLE 44

Synthesis of 6-Bromo-4-hydroxy-2,3,5-trimethylpivalanilide (25e).

By way of the same procedure that was used to deacetylate 23, crude 25d was isolated as a beige solid (86% yield) by deacetylation of 25c. It was dried and used in the next step without further purification. Spectral data: $^1$H NMR: δ 1.25 (s, 9H), 2.10 (s, 3H), 2.20 (s, 3H), 2.35 (s, 3H), 3.65 (br s, >1H, [H$_2$O]), 8.95 (s, 1H).

EXAMPLE 45

Synthesis of 6-Bromo-4-tert-butyldimethylsiloxy-2, 3,5-trimethylpivalanilide (25f).

Silylation of 25e was achieved by the method of Corey and Venkateswarlu, *J. Am. Chem. Soc.* 1972, 94, 6190. The crude material was obtained in 91% yield. Spectral data: $^1$H NMR: δ 0.20 (s, 6H), 1.00 (s, 9H), 1.25 (s, 9H), 2.05 (s, 3H), 2.15 (s, 3H), 2.25 (s, 3H), 8.95 (s, 1H).

EXAMPLE 46

Synthesis of N-Allyl-6-bromo-4-tert-butyldimethylsiloxy-2,3,5-trimethylpivalanilide (26)

Anilide 25f (15 g, 35 mmol) in tetrahydrofuran (400 mL) was added dropwise over 1 hour to a solution of allyl bromide (6 mL, 69 mmol) and previously washed and dried sodium hydride (1.68 g, 70 mmol) in tetrahydrofuran (50 mL). The latter solution was maintained at −20° C. during the addition process and subsequently allowed to approach ambient temperatures over 17 hours. It was quenched with ice water and the organic phase was then separated. The aqueous phase was washed with diethyl ether (3×75 mL), and the combined organic layers was washed with brine and dried (Na$_2$SO$_4$). Concentration afforded quantitative yields of a mustard-colored oil. Purification of this oil by flash column chromatography on silica gel using a solvent system of hexanes/ethyl acetate (9:1, R$_f$=0.26) afforded 26 (88% yield) as a colorless, viscous oil. Spectral data: $^1$H NMR: δ 0.15 (s, 6H), 0.95 (s, 9H), 1.05 (s, 9H), 2.15 (s, 3H), 2.20 (s, 3H), 2.30 (s, 3H), 3.70–3.80 (dd, 1H), 4.50–4.60 (dd, 1H), 5.00 (m, 2H), 5.85–6.05 (m, 1H).

EXAMPLE 47

Synthesis of N-Pivaloyl-5-hydroxy-3,4,6,7-tetramethylindole (27)

Indole 27 was prepared by the Pd-catalyzed cyclization of 26 according to the general procedure described earlier. The reaction temperature was maintained at 100° C. for 4.5–5 h and, after work-up, a waxy olive green residue was obtained. Purification was achieved by flash column chromatography on silica gel using a solvent system of increasing polarity (hexanes/ethyl acetate, 9:1, 8.5:1.5 and 8:2, $R_f$=0.30 in the last solvent system). The pure material, an amorphous white solid, mp 151.5°–153° C., was typically obtained in 40–45% yields. Spectral data: IR (Nujol) 3485, 1679, 1163 cm$^{-1}$; $^1$H NMR: (CD$_3$SOCD$_3$): δ 1.40 (s, 9H), 1.90 (s, 3H), 2.20 (s, 3H), 2.35 (s, 3H), 2.45 (s, 3H), 7.40 (s, 1H), 7.85 (s, 1H); $^{13}$C NMR (CD$_3$SOCD$_3$): δ 1.97, 3.16, 3.40, 7.56, 18.72, 31.14, 103.84, 106.77, 111.43, 111.92, 114.19, 118.08, 122.11, 139.03, 168.33; CI-MS: m/z 274 (MH$^+$, base), 256, 189; CI-HRMS (M+H$^+$): calcd. for C$_{17}$H$_{24}$NO$_2$ 274.1807, fnd. 274.1792. Anal: calcd. for C$_{17}$H$_{23}$NO$_2$ C, 74.69, H, 8.48, N, 5.12, fnd. C, 74.81, H, 8.49, N, 5.14.

EXAMPLE 48

Synthesis of 4-Acetoxy-2,3,5-trimethylacetanilide (28a).

Anilide 28a was prepared in 80% yield by the diacetylation of 4-hydroxy-2,3,5-trimethylaniline according to the method of Gilbert and Pinto, *J. Org. Chem.* 1992, 57, 5271–5276. The product precipitated from the organic layer during work-up and was collected as a white solid by vacuum filtration. It was vacuum-dried and used in the next step without further purification. Spectral data: $^1$H NMR (CD$_3$SOCD$_3$): δ 2.00 (3 partially resolved s, 12H), 2.35 (s, 3H), 7.00 (s, 1H), 9.38 (s, 1H); $^{13}$C NMR (CD$_3$SOCD$_3$): δ 13.01, 14.37, 15.82, 20.19, 23.01, 125.51, 126.53, 128.72, 130.33, 133.63, 145.25, 168.25, 168.73.

EXAMPLE 49

Synthesis of 4-Acetoxy-6-bromo-2,3,5-trimethylacetanilide (28b)

A solution of 28a (4.3 g, 18.2 mmol), bromine (1.8 mL, 36 mmol) and iron powder (0.27 g, 5 mmol) in glacial acetic acid (120 mL) was heated at 80° C. for 5 hours. The cooled reaction mixture was poured into ice-cold sodium bisulfite solution. The resulting fine white powder was isolated by vacuum filtration, washed with water and diethyl ether and dried at 60° C./0.2–0.5 torr. Anilide 28b was obtained in 80% yield and used without further purification. Spectral data: $^1$H NMR (CD$_3$SOCD$_3$): δ 1.90 (s, 3H), 2.00 (s, 3H), 2.10 (s, 3H), 2.20 (s, 3H), 2.35 (s, 3H), 9.55 (s, 1H); $^{13}$C NMR (CD$_3$SOCD$_3$): δ 13.21, 15.62, 17.29, 20.18, 22.46, 123.22, 127.67, 128.49, 133.28, 135.05, 146.28, 168.12, 168.64.

EXAMPLE 50

Synthesis of N-Allyl-4-acetoxy-6-bromo-2,3,5-trimethylacetanilide (28c)

The allylation of 28b was conducted in the same manner as for the allylation of 25f but with the following changes: dimethyl formamide was used in place of tetrahydrofuran, a 10- to 15-fold excess of allyl bromide was employed, the reaction was initiated and carried out at room temperature and over a 3-hour reaction time and, the dimethyl formamide was distilled from the reaction mixture before quenching. Pure 28b was obtained as a colorless oil (60% yield) after flash column chromatography over neutral alumina using a solvent system of Skellysolve B/ethyl acetate (7:3, $R_f$=0.27). Spectral data: $^1$H NMR (CD$_3$SOCD$_3$): δ 1.65 (s, 3H), 2.05 (s, 3H), 2.20 (s, 3H), 2.23 (s, 3H), 2.38 (s, 3H), 3.80–3.90 (dd, 1H), 4.30–4.40 (dd, 1H), 5.10 (m, 1H), 5.80–5.95 (m, 1H); $^{13}$C NMR (CD$_3$SOCD$_3$): δ 13.38, 16.09, 17.43, 20.18, 21.72, 50.64, 118.67, 124.00, 129.09, 129.87, 132.97, 135.75, 137.57, 147.17, 168.40, 169.14.

EXAMPLE 51

Synthesis of N-Acetyl-5-acetoxy-3,4,6,7-Tetramethylindoline (29a).

Cyclization of 28b and work-up of the reaction mixture was conducted analogously to that for the cyclization of 8. Pure 29a was obtained in 80% yield by purification of the crude material by flash column chromatography on silica gel using a solvent system of increasing polarity, namely, hexanes/ethyl acetate: 8:2, 6:4, 4:6, 2:8, $R_f$=0.35 in the last system. Spectral data: $^1$H NMR (CD$_3$SOCD$_3$): δ 1.10 (d, 3H), 1.95 and 1.96 (2 partially resolved s, 6H and 3H respectively), 2.20 (br s, 3H), 2.30 (s, 3H), 3.15–3.25 (m, 1H), 3.75–3.90 (br m, 1H), 3.90–4.05 (br m, 1H); $^{13}$C NMR (CD$_3$SOCD$_3$, 90° C., 500 MHz): δ 11.50, 12.17, 16.54, 17.48, 19.56, 22.57, 34.83, 58.06, 121.97, 124.86, 136.04, 138.37, 144.86, 168.01, 168.69.

EXAMPLE 52

Synthesis of N-Acetyl-5-hydroxy-3,4,6,7-tetramethylindoline (29b).

Deacetylation of 29a was achieved by reaction with potassium carbonate in methanol according to the procedure of Burkalova, et al., *Biofizika* 1980, 24, 989. Purification of crude material by flash column chromatography on silica gel using a solvent system of ethyl acetate/Skellysolve B (6:4, $R_f$=0.18) afforded 29b as a white solid, nap 171°–173° C. Spectral data: IR (Nujol) 3500, 1635, 1400, 1210 cm$^{-1}$; $^1$H NMR (CD$_3$SOCD$_3$): δ 1.05 (d, 3H), 1.90 (br s, 3H), 2.10 (2 partially resolved s, 3H each), 2.15 (br s, 3H), 3.10 (br m, 1H), 3.75 (br m, 1H), 3.85 (br m, 1H), 7.85 (br s, 1H); $^{13}$C NMR (CD$_3$SOCD$_3$): δ 12.34, 12.64, 17.42, 18.10, 23.50, 35.44, 58.25, 117.49, 121.94, 124.93, 133.47, 135.81, 150.41, 168.58; CI-MS: m/z 234 (MH$^+$, base), 172, 154, 136; CI-HRMS: Calcd. for C$_{14}$H$_{20}$NO$_2$ (M+H$^+$) 234.1494, fnd. 234.1494. Anal: calcd. for C$_{14}$H$_{19}$NO$_2$ C, 72.07, H, 8.21, N, 6.00, fnd. C, 71.85, H, 8.24, N, 5.92.

EXAMPLE 53

Synthesis of N-(2-Methyl-2-propenyl)-4-acetoxy-6-bromo-2,3,5-trimethylpivalanilide (30).

Methallylation of 25d was accomplished analogously to the allylation of 28b in dimethyl formamide. Flash column chromatography of the crude material on silica gel using a solvent system of Skellysolve B/ethyl acetate (60:40, $R_f$=0.30) afforded a clear colorless oil (65% yield). Spectral data: $^1$H NMR (CD$_3$SOCD$_3$): δ 1.65 (s, 3H), 1.75 (s, 3H), 2.05 (s, 3H), 2.20 (s, 3H), 2.25 (s, 3H), 2.40 (s, 3H), 3.65 (d, 1H), 4.35 (d, 1H), 4.60 (s, 1H), 4.70 (s, 1H).

EXAMPLE 54

Synthesis of N-Pivaloyl-5-acetoxy-3,3,4,6,7-pentamethylindoline (31a)

Indoline 31 a was prepared by the Pd-catalyzed cyclization of 30 according to the general procedure. The reaction was allowed to proceed at 85° C. for 14 h. Purification of the crude olive green waxy residue by flash column chromatography on silica gel using a solvent system of Skellysolve B and ethyl acetate (6:4, $R_f$=0.15) afforded a white solid (78% yield). Spectral data: $^1$H NMR: δ 1.35 (br s, 6H), 2.10 (s, 3H), 2.15 (s, 6H), 2.25 (br s, 3H), 2.35 (s, 3H), 3.70 (br s, 2H); CI-MS: m/z 290 (MH$^+$, base), 247, 205, 190, 174.

EXAMPLE 55

Synthesis of N-Pivaloyl-5-hydroxy-3,3,4,6,7-pentamethylindoline (31b)

Deacetylation of 31a was achieved as in the case of 29a. Product 31b was obtained as a white solid (79% yield), mp 164°–165° C. Spectral data: $^1$H NMR (CD$_3$SOCD$_3$): δ 1.25 (s, 6H), 1.90 (br s, 3H), 2.10 (s, 3H), 2.20 (s, 3H), 3.65 (br s, 2H), 7.85 (br s, 1H); $^{13}$C NMR (CD$_3$SOCD$_3$): δ 11.85, 12.75, 17.24, 23.41, 24.68, 42.57, 64.86, 117.90, 122.01, 124.93, 133.86, 137.71, 150.64, 168.32; CI-MS: m/z 248 (MH$^+$, base), 230, 205, 190, 167; CI-HRMS (M+H$^+$): Calcd. for C$_{15}$H$_{22}$NO$_2$ 248.1650, fnd. 248.1644. Anal: calcd. for C$_{15}$H$_{21}$NO$_2$ C, 72.7, H, 8.50, N, 5.70, fnd. C, 72.86, H, 8.46, N, 5.59.

EXAMPLE 56

Synthesis of Spiro[2,3-dihydro-5-hydroxy-4,6,7-trimethylbenzofuran-2,1'-cyclopropane] (32)

The phenol 32 was prepared according to the methods of Gilbert and Pinto, *J. Org. Chem.* 1992, 57, 5271.

EXAMPLE 57

Synthesis of 5-Hydroxy-2,4,6,7-tetramethylbenzofuran (33).

Phenol 33 was prepared by the reaction of Tebbe's reagent with 5-(tert-butyldimethylsiloxy)-4,6,7-trimethyl-2(3H)-benzofuranone according to the established procedure of Gilbert and Pinto, *J. Org. Chem.* 1992, 57, 5271. The exo-methylene compound so obtained was isomerized to the benzofuran by passing the crude mixture through a column of silica gel. The benzofuran was then recrystallized from hexanes and ethyl acetate (8:2) and sublimed at 50°–90° C. and at 0.51–0.5 torr, mp 136°–137° C. (lit.: Zahalka, H. A., et al., *J. Org. Chem.* 1988, 53, 3739–3745, 137.1°–138.9° C.). Spectral data: $^1$H NMR: a 2.25 (s, 3H), 2.30 (s, 3H), 2.40 (s, 3H), 2.42 (s, 3H), 4.40 (s, 1H), 6.28 (s, 1H); $^{13}$C NMR: δ 11.94, 12.03, 12.21, 14.16, 101.36, 110.18, 117.08, 118.21, 126.40, 147.23, 148.56, 154.41; EI-MS 190 (M$^+$, base), 189, 175, 43; HRMS: Calcd. for C$_{12}$H$_{14}$O$_2$ 190.0994, fnd. 190.0988.

Materials And Media

Cells were cultured in the following media: 1) MDA MB 435 cells were cultured in Minimum Essential Media (MEM-HyClone, Logan, Utah) supplemented with 5% heat inactivated fetal bovine serum (HyClone), 2 mM glutamine (Sigma, St. Louis, Mo.), 1 mM sodium pyruvate (Sigma), 1X MEM Non-Essential Amino Acids (Sigma), 2X MEM Vitamins (Sigma), and 100 IU/mL penicillin/100 µg/mL streptomycin (HyClone); 2) MCF-7 McGuire cells were cultured in Minimum Essential Media (MEM-HyClone, Logan, Utah) supplemented with 5% heat inactivated fetal bovine serum (HyClone), 2 mM glutamine (Sigma, St. Louis, Mo.), and 100 IU/mL penicillin/100 µg/mL streptomycin (HyClone); 3) HL-60 cells were cultured in Iscoves Modified Dulbecco's Media (IMDM-HyClone, Logan, Utah) supplemented with 5% heat inactivated fetal bovine serum (HyClone), 2 mM glutamine (Sigma, St. Louis, Mo.), 1 mM sodium pyruvate (Sigma), 1X MEM Non-Essential Amino Acids (Sigma), 2X MEM Vitamins (Sigma), and 100 IU/mL penicillin/100 µg/mL streptomycin (HyClone); 2) MCF-7 McGuire cells were cultured in Minimum Essential Media (MEM-HyClone, Logan, Utah) supplemented with 5% heat inactivated fetal bovine serum (HyClone), 2 mM glutamine (Sigma, St. Louis, Mo.), and 100 IU/mL penicillin/100 µg/mL streptomycin (HyClone); 3) HL-60 cells were cultured in Iscoves Modified Dulbecco's Media (IMDM-HyClone, Logan, Utah) supplemented with 5% heat inactivated fetal bovine serum (HyClone), 2 mM glutamine (Sigma, St. Louis, Mo.), and 100 IU/mL penicillin/100 µg/mL streptomycin (HyClone).

Solubility and Dilution of Phenolic Compounds

All compounds were handled as if they were light sensitive. All compounds were initially dissolved in absolute ethanol and subsequently diluted to a final concentration of 0.5% ethanol with the appropriate medium.

EXAMPLE 58

Bioassay

For the bioassay, all cells were used at 2.5×10$^5$/mL. Cells were treated with each of the compounds at concentrations of 20, 10, 5, 1, 0.1, and 0.01 µg/mL, and 200 µl of each treatment group were plated in quadruplicate in a 96 well culture plate (Corning, Corning N.Y.). Plates were done in duplicate, one plate to be used for viability testing and the other plate to examine $^3$H-TdR uptake (DNA synthesis).

Plates were cultured for 48 hours at 37° C., 5% CO$_2$. Eight hours prior to the end of incubation, $^3$H-TdR was added to one of the duplicate plates and incubation continued for 8 hours. The cells were then harvested (trypsinization was required to harvest MDA MB 435 and MCF-7 McGuire). At the end of the incubation, the cells were removed from the wells (of the duplicate plate—no radioisotope added) and viability checked by the Trypan Blue Exclusion method. Percent viability and percent suppression of each treatment group were calculated.

EXAMPLE 59

Antiproliferative Effects

With respect to the data shown in the Tables below, the data is arranged from greatest percent inhibition of DNA synthesis to lowest. "TOXIC" refers to the fact that the compound at this concentration killed the cells or greatly lowered their viability. "NT" refers to "Not Tested". The cells were cultured for 48 hours, pulsed 8 hours with tritiated thymidine, harvested and counted. MDA MB 435 is the abbreviation for the Metastic Human Breast Cancer Cell Line. MCF-7 McGuire is the abbreviation for the Estrogen Responsive Human Breast Cancer Cell Line and HL-60 is the Human Promyelocytic Leukemia Cell Line.

Table I shows that compound 27 (MP2.8) significantly inhibited the proliferation of MB-435, MCF-7 and HL-60 cells at a dose of 5 µg/mL. Table II shows that compound 24 (MP2.1) significantly inhibited the proliferation of MB-435 and MCF-7 cells at 10 µg/mL and HL-60 cells at a dose of 20 µg/mL. Table III shows that compound 6 (KJA1) significantly inhibited the proliferation of MCF-7 and HL-60 cells at 10 µg/mL, and MB-435 cells at 5 µg/mL. Table IV shows that compound 13 (K-IPMP) inhibited the proliferation of MB-435 and HL-60 cells at 20 µg/mL. Table V shows that compound 12b (K-IPPA) significantly inhibited the proliferation of MB-435, MCF-7 and HL-60 cells at a dose of 5–20 µg/mL.

TABLE I

INHIBITION (%) OF DNA SYNTHESIS BY COMPOUND 27 (MP2.8)
Concentration of Compounds (µg/mL)

| Cell Type | 20 | 10 | 5 | 1 | 0.1 | 0.01 |
|---|---|---|---|---|---|---|
| MB-435 | 97 | 91 | 54 | 15 | 4 | NT |
| MCF-7 | TX | 86 | 57 | 14 | 0 | NT |
| HL-60 | 97 | 91 | 61 | 12 | 0 | NT |

TABLE II

INHIBITION (%) OF DNA SYNTHESIS BY COMPOUND 24 (MP 2.1)
Concentration of Compounds (µg/mL)

| Cell Type | 20 | 10 | 5 | 1 | 0.1 | 0.01 |
|---|---|---|---|---|---|---|
| MB-435 | 97 | 85 | 29 | 5 | 13 | NT |
| MCF-7 | 97 | 85 | 25 | 4 | 0 | NT |
| HL-60 | 47 | 30 | 5 | 0 | 7 | NT |

TABLE III

INHIBITION (%) OF DNA SYNTHESIS BY COMPOUND 6 (KJA1)
Concentration of Compounds (µg/mL)

| Cell Type | 20 | 10 | 5 | 1 | 0.1 | 0.01 |
|---|---|---|---|---|---|---|
| MB-435 | TOXIC | TOXIC | 80 | 0 | 3 | NT |
| MCF-7 | TOXIC | 37 | 13 | 10 | 0 | NT |
| HL-60 | TOXIC | 89 | 59 | 24 | 3 | NT |

TABLE IV

INHIBITION (%) OF DNA SYNTHESIS BY COMPOUND 13 (K-IPMP)
Concentration of Compounds (µg/mL)

| Cell Type | 20 | 10 | 5 | 1 | 0.1 | 0.01 |
|---|---|---|---|---|---|---|
| MB-435 | 45 | 17 | 8 | −4 | 4 | NT |
| MCF-7 | NT | NT | NT | NT | NT | NT |
| HL-60 | 53 | 27 | 15 | 10 | 0 | NT |

TABLE V

INHIBITION (%) OF DNA SYNTHESIS BY COMPOUND 12b (K-IPPA)
Concentration of Compounds (µg/mL)

| Cell Type | 20 | 10 | 5 | 1 | 0.1 | 0.01 |
|---|---|---|---|---|---|---|
| MB-435 | 41 | 24 | 32 | 19 | 1 | NT |
| MCF-7 | 70 | 58 | 38 | 47 | 20 | NT |
| HL-60 | 46 | 67 | 32 | 2 | 0 | NT |

EXAMPLE 60

Table VI shows that compound 33 (MP2.6) significantly inhibited the proliferation of MB-435, MCF-7 and HL-60 cells at a dose of 20 µg/mL Table VII shows that compound 11 b (K-IPP) significantly inhibited the proliferation of MB-435 cells at 10 µg/mL and MCF-7 cells at 5 µg/mL, while having virtually no effect on HL-60 cells. Table VIII shows that compound 6 (KJA1) significantly inhibited the proliferation of MB-435 and MCF-7 cells at 10–20 µg/mL, while having virtually no effect on HL-60 cells. Table IX shows that compound 32 (MP2.5) significantly inhibited the proliferation of MB-435, MCF-7 and HL-60 cells at a dose of 10–20 µg/mL. Table X shows that compound 20 (K-TBDP) inhibited the proliferation of MB-435 and HL-60 cells at 20 µg/mL; MCF-7 cells were not tested with this compound. Table XI shows that compound 31b (MP2.9) significantly inhibited the proliferation of MB-435, MCF-7 and HL-60 cells at a dose of 10–20 µg/mL. Table XII shows that compound 16 (K-ADMP) significantly inhibited the proliferation of MB-435 and HL-60 cells at 5–20 µg/mL; MCF-7 cells were not tested with this compound.

TABLE VI

INHIBITION (%) OF DNA SYNTHESIS BY COMPOUND 33 (MP2.6)
Concentration of Compounds (µg/mL)

| Cell Type | 20 | 10 | 5 | 1 | 0.1 | 0.01 |
|---|---|---|---|---|---|---|
| MB-435 | 42 | 16 | 8 | 2 | 1 | NT |
| MCF-7 | 72 | 16 | 0 | 0 | 19 | NT |
| HL-60 | 36 | 7 | 0 | 0 | 0 | NT |

TABLE VII

INHIBITION (%) OF DNA SYNTHESIS BY COMPOUND 11b (K-IPP)
Concentration of Compounds (µg/mL)

| Cell Type | 20 | 10 | 5 | 1 | 0.1 | 0.01 |
|---|---|---|---|---|---|---|
| MB-435 | 36 | 22 | 21 | 21 | 0 | NT |
| MCF-7 | 53 | 33 | 47 | 26 | 24 | NT |
| HL-60 | 0 | 0 | 0 | 0 | 0 | NT |

TABLE VIII

INHIBITION (%) OF DNA SYNTHESIS BY COMPOUND 11c (K-TBP)
Concentration of Compounds (µg/mL)

| Cell Type | 20 | 10 | 5 | 1 | 0.1 | 0.01 |
|---|---|---|---|---|---|---|
| MB-435 | 31 | 12 | 20 | 12 | 13 | NT |
| MCF-7 | 43 | 31 | 9 | 1 | 18 | NT |
| HL-60 | 0 | 0 | 0 | 0 | 0 | NT |

TABLE IX

INHIBITION (%) OF DNA SYNTHESIS BY COMPOUND 32 (MP2.5)
Concentration of Compounds (µg/mL)

| Cell Type | 20 | 10 | 5 | 1 | 0.1 | 0.01 |
|---|---|---|---|---|---|---|
| MB-435 | 43 | 30 | 15 | 6 | 6 | NT |
| MCF-7 | 22 | 18 | 5 | 10 | 0 | NT |
| HL-60 | 26 | 17 | 12 | 5 | 11 | NT |

TABLE X

INHIBITION (%) OF DNA SYNTHESIS BY COMPOUND 20 (K-TBDP)
Concentration of Compounds (µg/mL)

| Cell Type | 20 | 10 | 5 | 1 | 0.1 | 0.01 |
|---|---|---|---|---|---|---|
| MB-435 | 31 | −13 | −1 | −5 | −1 | NT |
| MCF-7 | NT | NT | NT | NT | NT | NT |
| HL-60 | 63 | 33 | 18 | 6 | 2 | NT |

TABLE XI

INHIBITION (%) OF DNA SYNTHESIS BY COMPOUND 31b (MP2.9)
Concentration of Compounds (μg/mL)

| Cell Type | 20 | 10 | 5 | 1 | 0.1 | 0.01 |
|---|---|---|---|---|---|---|
| MB-435 | 33 | 15 | 0 | –0 | 0 | NT |
| MCF-7 | 22 | 18 | 29 | 0 | 0 | NT |
| HL-60 | 28 | 15 | 6 | 0 | 0 | NT |

TABLE XII

INHIBITION (%) OF DNA SYNTHESIS BY COMPOUND 16 (K-ADMP)
Concentration of Compounds (μg/mL)

| Cell Type | 20 | 10 | 5 | 1 | 0.1 | 0.01 |
|---|---|---|---|---|---|---|
| MB-435 | 31 | 18 | 9 | 1 | 0 | NT |
| MCF-7 | NT | NT | NT | NT | NT | NT |
| HL-60 | 15 | 11 | 11 | 0 | 0 | NT |

EXAMPLE 61

The present invention has potential for the efficacy of 5-hydroxyindoles and 5-hydroxy-2,3-dihydroindole derivatives of the present invention as therapeutic agents by in vivo analyses of immune status and health of chickens inoculated with arian erythroblastosis virus or arian erythroblastosis virus-transformed tumor cells.

Avian Erythroblastosis Virus (AEV) Model

The in vivo studies utilize an avian retrovirus erythroleukemia model, namely, the avian erythroblastosis virus model. The arian erythroblastosis virus causes a rapid cachexia and fatal leukemia in 100% of challenged young birds. Newly hatched chickens are fed the 5-hydroxyindoles and 5-hydroxy-2,3-dihydroindole derivatives of the present invention supplemented diets or are intraperitoneally injected daily with the 5-hydroxyindoles and 5-hydroxy-2, 3-dihydroindole derivatives of the present invention for one week prior to tumor induction. For tumor induction, the chickens are injected with erythroleukemia cells or infectious arian erythroblastosis virus and their health (weight, immune status, red blood cell status, e.g., anemia, and viability) are monitored.

EXAMPLE 62

Supplementation with 27 (MP2.8)

The maximum level of the 5-hydroxyindole derivative 27 (MP 2.8) that can be fed or injected without negatively affecting the health and growth of chickens is being established. These studies will also measure levels of 27 in the serum. Newly hatched SC strain White Leghorn chickens from Hy-line International (Dallas Center, IA) are to be used. Upon arrival the chicks will be assigned randomly (10/group/brooder). Chicks will be housed in thermostatically controlled battery brooders with raised wire floors modified to prevent the loss of feed and are given a 15-hour day (15 hours light, 9 hours dark).

The chickens will be observed daily and food consumption (brooder average values) will be determined every other day. Body weights will be determined three times/week by weighing chicks. Blood (plasma) will be taken at weekly intervals, hematocrits will be performed and hexane extracts prepared and analyzed for the 5-hydroxyindole derivative 27, using high-performance liquid chromatography. At the conclusion of the study, chickens will be sacrificed by carbon dioxide anesthesia performed in compliance with recommendations of the Panel on Euthanasia of the American Veterinary Medical Association. Internal organs will be examined for any type of gross morphological evidence of 27 toxicity. The content of 27 in splenic bursal and thymic lymphocytes will be determined after density gradient purification and saponification and extraction into hexane by HPLC. These studies will permit the determination of levels of MP 2.8 that can be administered to young chicks, and determine the levels of MP 2.8 found in plasma, peripheral blood red blood cells, splenic, bursal, and thymic lymphoid cells of chickens.

EXAMPLE 63

Analyses of Health of Chickens Challenged with AEV

Upon arrival newly hatched chicks (10 chickens/group/brooder) will be assigned randomly to control groups and groups supplemented with 27. Eight days later (day 10 post hatch), control chicks and those supplemented with 27 will be challenged with intravenous injections of $2.5 \times 10^5$ FFU AEV in 0.2 mL volume of phosphate buffered saline/animal or $1 \times 10^4$ AEV tumor cells in 0.2 mL volume of phosphate buffered saline per animal. Previous studies have shown that this dose of virus or tumor cells when injected into chickens less than five weeks of age, induces fatal erythroleukemia involving weight loss, thymic atrophy and immune suppression in 100% of the chickens within 3 weeks. (Rao, A., Kline, K., and Sanders, B. G. Immune Abnormalities in Avian Erythroblastosis Virus-Infected Chickens. Cancer Research 50: 4764–4770, 1990). The general health of the chickens will be observed daily, and body weight of individual chickens will be measured two times per week. Initially, tumor progression will be determined by comparing the time of death of virally and tumor injected chickens in non-27 supplemented controls versus 27-supplemented groups. The day of death is recorded as the day a chicken dies or is sacrificed in moribund condition.

Generally, 10–14 days following virus or tumor injection, all virus or tumor injected non-27 supplemented control chickens are dead. Supplementations with 27 will continue until control animals die (permitting evaluation of the ability of 27 to prolong life) or until an animal is judged to be tumor free based on ability to survive 4 weeks beyond expected time of death with no histological evidence of erythroleukemia. At this time supplementation with 27 is terminated. These chickens are observed for general health, and body weights, and are assessed weekly for another four weeks when the experiment is terminated.

If supplementations with 27 diminish or prevent lethal erythroleukemia, additional experiments is conducted to determine if 27 supplementation reduces cachexia (prevents weight loss, anemia, and immune suppression). Thus, 27 supplemented virus injected chickens and controls is used. Weights are measured every other day. Starting at 6 days post-virus injection and every other day until day 14, five chickens from control and treatment groups are sacrificed by carbon dioxide anesthesia, bled for hematological analyses and spleen and thymus removed for immune analyses. The immune status is analyzed using standard T cell lectin-induced mitogenesis and standard co-culture analyses for the presence of T suppressor cell activity.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. An antiproliferative p-heteroatom-substituted phenol compound, or derivative thereof, having a structural formula

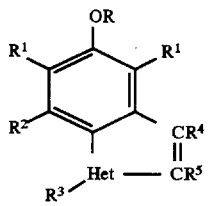

wherein Het is nitrogen, oxygen or sulfur, wherein when Het=O, $R^1$ is an alkyl group other than methyl or t-butyl;

wherein R is selected from the group consisting of hydrogen, alkyl, arylmethyl and acyl;

$R^1$ is alkyl;

$R^2$ is selected from the group consisting of hydrogen and alkyl;

$R^3$ is selected from the group consisting of alkyl and acyl when Het is nitrogen,: (electron pair) when Het is oxygen or sulfur;

$R^4$ is selected from the group consisting of hydrogen and alkyl; and $R^5$ is selected from the group consisting of hydrogen and alkyl.

2. The compound of claim 1 having the chemical name of N-Pivaloyl-5-hydroxy-3,4,6,7-tetramethylindole.

3. The compound of claim 1, having the chemical name of N-isobutyryl-5-methoxy-3,4,6-trimethylindoline.

4. The compound of claim 1, having the chemical name of N-isobutyryl-5 -acetoxy-3,4,6-trimethylindoline.

5. An antiproliferative compound having the chemical name of 5-hydroxy-2,4,6,7-tetramethylbenzofuran.

6. The compound of claim 1, having the chemical name of N-isobutyryl-5-hydroxy-3,4,6-trimethylindoline.

7. A pharmaceutical composition, comprising the compound of claim 1 and a pharmaceutically acceptable carrier.

8. A pharmaceutical composition comprising a compound selected from the group consisting of N-pivaloyl-5-hydroxy-3,4,6,7-tetramethylindole, 4,6-di-tert-butyl-2,3-dihydro-5-hydroxy-2-(3H)-benzofuranone, N-isobutyryl-5-methoxy-3,4,6-trimethylindoline, N-isobutyryl-5-acetoxy-3,4,6-trimethylindoline, 5-hydroxy-2,4,6,7-tetramethylbenzofuran, N-isobutyryl-5-hydroxy-3,4,6-trimethylindoline and 9-acetoxy-8,10-dimethyljulolidine.

9. An antiproliferative p-heteroatom-substituted phenol compound, or derivative thereof, having a structural formula

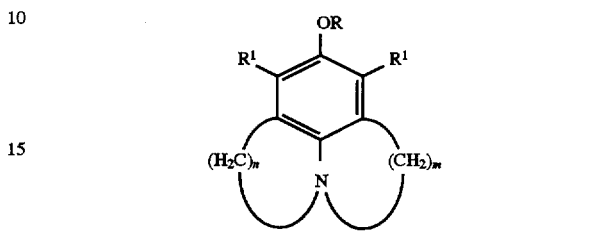

wherein m is 2 to 4 and n is 2 to 4;

wherein R is selected from the group consisting of hydrogen, alkyl, arylmethyl and acyl;

$R^1$ is alkyl.

10. The compound of claim 9, having the chemical name of 9-acetoxy-8,10-dimethyljulolidine.

11. A pharmaceutical composition, comprising the compound of claim 9 and a pharmaceutically acceptable carrier.

12. An antiproliferative compound having the chemical name of 4,6-di-tert-butyl-2,3-dihydro-5-hydroxy-2-(3H)-benzofuranone.

13. A method for the treatment of breast cancer or leukemia comprising administering to an animal a pharmacologically and therapeutically effective dose of a pharmaceutical composition comprising a p-heteroatom-substituted phenol of claim 1 or claim 9.

14. The method of claim 13, wherein said animal is a human.

15. The method of claim 13, wherein said composition is administered in a dose of from about 1 mg/kg to about 60 mg/kg.

16. The method of claim 13, wherein said composition is administered orally.

17. A method for the treatment of breast cancer or leukemia comprising administering to an animal a pharmacologically and therapeutically effective dose of a pharmaceutical composition comprising a compound selected from the group consisting of N-pivaloyl-5-hydroxy-3,4,6,7-tetramethylindole, 4,6-di-tert-butyl-2,3-dihydro-5-hydroxy-2-(3H)-benzofuranone, N-isobutyryl-5-methoxy-3,4,6-trimethylindoline, N-isobutyryl-5-acetoxy-3,4,6-trimethylindoline, 5-hydroxy-2,4,6,7-tetramethylbenzofuran, N-isobutyryl-5-hydroxy-3,4,6-trimethylindoline and 9-acetoxy-8,10-dimethyljulolidine.

* * * * *

UNITED STATES PATENT AND TRADEMARK OFFICE
CERTIFICATE OF CORRECTION

PATENT NO. : 5,674,876  
DATED : October 7, 1997  
INVENTOR(S) : Gilbert et al.

Page 1 of 6

It is certified that error appears in the above-identified patent and that said Letters Patent is hereby corrected as shown below:

Column 1,  
Line 10, "p-heteroatom-substituted" should read -- *p*-heteroatom --.

Column 2,  
Line 9, please italicize "meta-, para-, para-, and para-".

Column 3,  
Lines 1, 21 and 24, "p-heteroatom" should read -- *p*-heteroatom --.  
Line 25, "derivative sthereof" should read -- derivatives thereof --.  
Line 28, please remove the period between the numbers "8" and "10" and replace it with a comma.  
Line 31, "(lib)" should read -- (11b) --.  
Line 31, "N-pivaloyl-" should read -- *N*-pivaloyl- --.  
Lines 32 and 33, "N-isobutyryl-" should read -- *N*-isobutyryl- --.  
Line 36, "N-acetyl-" should read -- *N*-acetyl- --.  
Line 38, "N-pivaloyl-" should read -- *N*-pivaloyl- --.  
Line 40, "tert" should read -- *tert* --.  
Line 40, "H-" at the end of the line should read -- *H*- --.  
Lines 44, 46 and 48, please italicize the "N" at the beginning of the line.  
Line 53, "p-heteroatom," should read -- *p*-heteroatom --.  
Line 67, "(HL-60))" should read -- (HL-60) --.

Column 4,  
Line 3, please italicize "inter alia".  
Lines 23, 25, 28 and 30, "p-heteroatom" should read "*p*-heteroatom".  
Line 32, "N-pivaloyl-5-" should read -- *N*-pivaloyl-5- --.  
Line 34, "H-benzofuranone" should read -- *H*-benzofuranone --.  
Lines 35, 36 and 38, "N-isobutyryl" should read -- *N*-isobutyryl --.

Column 5,  
Lines 21, 24, 29, 32, 36, 37, 45, 55 and 67, "p-heteroatom" should read -- *p*-heteroatom --.

Column 6,  
Lines 5 and 51, "p-Heteroatom" should read -- *p*-heteroatom --.  
Line 12, "p-heteroatom" should read -- *p*-heteroatom --.  
Line 67, delete the word "were" and replace it with "was".

UNITED STATES PATENT AND TRADEMARK OFFICE
CERTIFICATE OF CORRECTION

PATENT NO. : 5,674,876
DATED : October 7, 1997
INVENTOR(S) : Gilbert et al.

It is certified that error appears in the above-identified patent and that said Letters Patent is hereby corrected as shown below:

Column 7,
Line 1, "(2)" should read -- (2) --.
Line 7, "(1, 61 g. 500 mmol)" should read -- (1, 61 g. 500 mmol) --.
Line 14, "(2, 39g" should read -- (2, 39g --.
Line 21, "(3)" should read -- (3) --.
Line 22, "(2, 36 g. 260 mmol)" should read -- (2, 36 g. 260 mmol) --.
Line 28, "(3," should read -- (3, --.
Lines 34 and 42, "(4)" should read -- (4) --.
Line 36, "(3, 29 g. 160 mmol)" should read -- (3, 29 g. 160 mmol) --.
Line 47, "(5)" should read -- (5) --.
Line 49, "(4, 1.4 g. 9.3 mmol)" should read -- (4, 1.4 g. 9.3 mmol) --.
Line 63, "(5, 1.2 g." should read -- (5, 1.2 g. --.

Column 8,
Line 6, "(5, 109 mg. 0.5" should read -- (5, 109 mg. 0.5 --.
Line 14, "J=6.8" should read -- *J*=6.8 --.
Line 14, "J=6.6" should read -- *J*=6.6 --.
Line 20, "(6)" should read -- (6) --.
Line 34, "(6, 680 mg. 94%" should read -- (6, 680 mg. 94% --.
Line 36, "J=7" should read -- *J*=7 --.
Line 37, "J=5" should read -- J=5 --.
Line 43, "(7)" should read -- (7) --.
Line 45, "(4, 5g. 33.2 mmol) should read -- (4, 5g. 33.2 mmol) --.
Line 55, "(7, 5.3 g. 83% yield)" should read -- (7, 5.3 g. 835 yield) --.
Line 65, "(7, 8.6 g. 44.3 mmol)" should read -- (7, 8.6 g. 44.3 mmol) --.

Column 9,
Line 18, "N-Allyl" should read -- *N*-Allyl --.
Line 19, "(8)" should read "(8)".
Line 36, "(8, 8.7 g. 85% yield)" should read -- (8, 8.7 g. 85% yield) --.

Column 10,
Line 20, "N-Acetyl" should read -- *N*-Acetyl --.
Line 21, "(12a)" should read -- (12a) --.
Line 33, "12a" should read -- 12a --.
Line 63, "(10)" should read -- (10) --.

UNITED STATES PATENT AND TRADEMARK OFFICE
CERTIFICATE OF CORRECTION

PATENT NO. : 5,674,876  
DATED : October 7, 1997  
INVENTOR(S) : Gilbert et al.

It is certified that error appears in the above-identified patent and that said Letters Patent is hereby corrected as shown below:

Column 11,  
Lines 13, 37 and 61, "N-Isobutyryl" should read -- *N*-Isobutyryl --.  
Lines 14 and 24, "(11b)" should read -- (11b) --.  
Line 15, "10" should read -- 10 --.  
Line 27, "J=6.5" should read -- *J*=6.5 --.  
Line 28, "J=10" should read -- *J*=10 --.  
Line 38, "(12b)" should read -- (12b) --.  
Lines 41, "(11b" should read -- (11b --.  
Lines 51 and 66, "N-isobutyryl" should read -- "*N*-isobutyryl --.  
Line 52, "(12b," should read -- (12b, --.  
Line 54, "J=6.7" should read -- *J*=6.7 --.  
Line 55, "J=10.2" should read -- *J*=10.2 --.  
Line 62, "(13)" should read -- (13) --.  
Line 67, "(11b," should read -- (11b, --.

Column 12,  
Line 10, "N-isobutyryl" should read -- *N*-isobutyryl --.  
Line 10, "(13," should read -- (13, --.  
Line 13, in both places "J=6.5" should read -- *J*=6.5 --.  
Line 18, "N-Pivaloyl" should read -- *N*-Pivaloyl --.  
Line 19, "(11c)" should read -- (11c) --.  
Line 20, "10" should read -- 10 --.  
Line 21, "11b" should read -- 11b --.  
Line 23, "11c" should read -- 11c --.  
Line 32, "N-(2-Methyl" should read -- *N*-(2-Methyl --.  
Line 33, "(14)" should read -- (14) --.  
Line 36, "8," should read -- 8, --.  
Line 37, "14" should read -- 14 --.  
Line 39, "J=15" should read -- *J*=15 --.  
Line 44, "palladium" should read -- Palladium --.  
Line 60, please insert a period at the end of the sentence.  
Line 63, "N-Acetyl" should read -- *N*-Acetyl --.  
Line 64, "(15)" should read -- (15) --.

UNITED STATES PATENT AND TRADEMARK OFFICE
CERTIFICATE OF CORRECTION

PATENT NO.    : 5,674,876
DATED         : October 7, 1997
INVENTOR(S)   : Gilbert et al.

It is certified that error appears in the above-identified patent and that said Letters Patent is hereby corrected as shown below:

Column 13,
Line 1, "15" should read -- 15 --.
Line 8, "N-Acetyl" should read -- *N*-Acetyl --.
Line 9, "(16)" should read -- (16) --.
Line 11, "15" should read -- 15 --.
Line 12, "11a" and "16" should read -- 11a -- and -- 16 --.
Lines 21, 37 and 57, "N-Pivaloyl" should read -- *N*-Pivaloyl --.
Line 24, "4" should read -- 4 --.
Line 38, "(17)" should read -- (17) --.
Lines 51 and 63, "119" should read -- 119 --.
Line 57, "N-(2-Methyl" should read -- *N*-(2-Methyl --.

Column 14,
Lines 16 and 44, "N-Pivaloyl" should read -- *N*-Pivaloyl --.
Line 17, "(19)" should read -- (19) --.
Line 19, "18" should read -- 18 --.
Line 20, "19" should read -- 19 --.
Line 45, "(20)" should read -- (20) --.
Line 50, "N-isobutyryl" should read -- *N*-isobutyryl --.
Line 51, "11b" and "20" should read -- 11b -- and -- 20 --.
Line 61, "tert" should read -- *tert* --.

Column 17,
Line 38, "Example 41" should read -- Example 40 --.
Line 57, "Example 42 should read -- Example 41 --.

Column 18,
Line 6, "Example 43" should read -- Example 42 --.
Line 23, "Example 44" should read -- Example 43 --.
Line 34, "Example 45" should read -- Example 44 --.
Line 44, "Example 46" should read -- Example 45 --.
Line 59, "was" should read -- were --.

UNITED STATES PATENT AND TRADEMARK OFFICE
CERTIFICATE OF CORRECTION

PATENT NO. : 5,674,876
DATED : October 7, 1997
INVENTOR(S) : Gilbert et al.

It is certified that error appears in the above-identified patent and that said Letters Patent is hereby corrected as shown below:

Column 19,
Line 1, "Example 47" should read -- Example 46 --.
Line 24, "Example 48" should read -- Example 47 --.
Line 41, "Example 49" should read -- Example 48 --.
Line 59, "Example 50" should read -- Example 49 --.
Line 65, please delete the comma between the words "tetrahydrofuran" and "a" and insert a semi-colon.

Column 20,
Line 1, "time and" should read -- time, and, --.
Line 13, "Example 51" should read -- Example 50 --.
Line 30, "Example 52" should read -- Example 51 --.
Line 39, "nap" should read -- mp --.
Line 50, "Example 53" should read -- Example 52 --.
Line 63, "Example 54" should read -- Example 53 --.

Column 21,
Line 8, "Example 55" should read -- Example 54 --.
Line 25, "Example 56" should read -- Example 55 --.
Line 32, "Example 57" should read -- Example 56 --.
Line 24, "Example 58, should read -- Example 57 --.
Line 46, "Example 59" should read -- Example 58 --.

Column 23,
Line 58, "Example 60" should read -- Example 59 --.

Column 25,
Line 23, "Example 61" should read -- Example 60 --.
Line 48, "Example 62" should read -- Example 61 --.

UNITED STATES PATENT AND TRADEMARK OFFICE
CERTIFICATE OF CORRECTION

PATENT NO. : 5,674,876
DATED : October 7, 1997
INVENTOR(S) : Gilbert et al.

It is certified that error appears in the above-identified patent and that said Letters Patent is hereby corrected as shown below:

Column 26,
Line 16, "Example 63" should read -- Example 62 --.
Line 46, please insert a hyphen after the word "tumor" at the end of the line.
Lines 54 and 57, "is" should read -- are --.

Signed and Sealed this

Twenty-seventh Day of November, 2001

Attest:

*Nicholas P. Godici*

NICHOLAS P. GODICI
*Attesting Officer*   *Acting Director of the United States Patent and Trademark Office*